(12) United States Patent
Post et al.

(10) Patent No.: US 12,146,161 B2
(45) Date of Patent: *Nov. 19, 2024

(54) MAMMALIAN ALVEOLAR MACROPHAGES DERIVED FROM PLURIPOTENT CELLS

(71) Applicant: The Hospital for Sick Children, Toronto (CA)

(72) Inventors: Martin Post, Toronto (CA); Michael Litvack, Toronto (CA)

(73) Assignee: The Hosptial for Sick Children, Toronto (CA)

( * ) Notice: Subject to any disclaimer, the term of this patent is extended or adjusted under 35 U.S.C. 154(b) by 790 days.

This patent is subject to a terminal disclaimer.

(21) Appl. No.: 17/316,060

(22) Filed: May 10, 2021

(65) Prior Publication Data

US 2021/0301256 A1  Sep. 30, 2021

Related U.S. Application Data

(63) Continuation-in-part of application No. 15/672,432, filed on Aug. 9, 2017, now Pat. No. 11,001,806, which is a continuation-in-part of application No. PCT/CA2016/050128, filed on Feb. 11, 2016.

(60) Provisional application No. 62/114,851, filed on Feb. 11, 2015.

(51) Int. Cl.
| | |
|---|---|
| C12N 5/00 | (2006.01) |
| A61K 39/00 | (2006.01) |
| C07K 14/54 | (2006.01) |
| C07K 14/81 | (2006.01) |
| C12N 5/0786 | (2010.01) |

(52) U.S. Cl.
CPC ........ *C12N 5/0645* (2013.01); *A61K 39/4614* (2023.05); *A61K 39/4622* (2023.05); *A61K 39/4635* (2023.05); *A61K 39/464* (2023.05); *C07K 14/5428* (2013.01); *C07K 14/8125* (2013.01); *A61K 2239/31* (2023.05); *A61K 2239/38* (2023.05); *C12N 2501/125* (2013.01); *C12N 2501/165* (2013.01); *C12N 2501/22* (2013.01); *C12N 2501/2303* (2013.01); *C12N 2501/2306* (2013.01)

(58) Field of Classification Search
None
See application file for complete search history.

(56) References Cited

U.S. PATENT DOCUMENTS

| | | | |
|---|---|---|---|
| 9,745,553 | B2 | 8/2017 | Keller et al. |
| 9,834,754 | B2 | 12/2017 | Keller et al. |
| 9,994,821 | B2 | 6/2018 | Keller et al. |
| 11,001,806 | B2 * | 5/2021 | Post ........................ A61K 35/15 |
| 2009/0017539 | A1 | 1/2009 | Spanholtz |
| 2014/0322808 | A1 | 10/2014 | Keller et al. |

FOREIGN PATENT DOCUMENTS

| | | |
|---|---|---|
| EP | 2647698 | 10/2013 |
| WO | 2009/104825 | 8/2009 |
| WO | 2014/012933 | 1/2014 |
| WO | 2017/097876 | 6/2017 |

OTHER PUBLICATIONS

International Search Report—PCT/CA2016/050128 dated Apr. 26, 2021.
Suzuki et al.—"Pulmonary Macrophage Transplation", Nature Oct. 23, 2014 (Oct. 23, 2014) vo. 574, No. 7523 pp. 450-454 ISSN: 0028-0836.
Happle et al.—"Pulmonary transplation of macrophage progenitors as effective and long-lasting therapy for hereditary pulmonary alveolar proteinosis", Science Translational Medicine Aug. 20, 2014 (Aug. 20, 2014), vol. 6, No. 250, p. 25 Oral 113, ISSN:1946-6234.
Suzuki et al.—"Use of Induced Pluripotent Stem Cells to Recapitulate Pulmonary Alveolar Proteinosis Pathogenisis", American Journal of Respiratory and Critical Care Medicine, Jan. 15, 2014 (Jan. 15, 2014), vol. 189, No. 2, pp. 183-193, ISSN:1073-449X.
Van Wilgenburg et al.—"Efficient, Long Term Production of Monocyte-Derived Macrophages from Human Pluripotent Stem Cells under Partly-Defined and Fully-Defined Conditions", Plos One, Aug. 12, 2013(Aug. 12, 2013), vol. 8, No. 8, p. 71098, ISSN: 1932-6203.
Achmann et al.—"Gene Correction of Human Induced Pluripotent Stem Cells Repairs the Cellular Phenotype in Pulmonary Alveolar Proteinosis", American Journal of Respiratory and Critical Care Medicine Jan. 15, 2014 (Jan. 15, 2014), vol. 189, No. 2, pp. 167-183 ISSN: 1073-449X.
Lu et al.—"Generation of functional hemangioblasts from human embryonic stem cells" Nature Methods Jun. 2007 (Jun. 2007), vol. 4, No. 6, pp. 501-209, ISSN: 1548-7091.
Gomez-Perdiguero et al.—"Tissue-resident macrophages originate from yolk-sac-derived erythro-myeloid progenitors", Nature Feb. 26, 2015 (Feb. 26, 2015) E pub, Dec. 3, 2014 (Dec. 3, 2014), vol. 518, No. 7540, pp. 547-551 ISSN:0028-0836.

(Continued)

*Primary Examiner* — Michael C Wilson

(74) *Attorney, Agent, or Firm* — Gowling WLG (Canada) LLP

(57) ABSTRACT

Alveolar-like macrophages and a method for generating alveolar-like macrophages from hemangioblasts is provided. The method comprises the steps of: i) culturing the hemangioblasts in a hematopoietic-inducing medium comprising vascular endothelial growth factor (VEGF), stem cell factor (SCF) and interleukin-3 (IL-3) for a sufficient period of time to generate macrophages, and ii) culturing the macrophages in an alveolar macrophage-inducing medium comprising granulocyte macrophage colony stimulating factor (GM-CSF), and optionally macrophage colony stimulating factor (M-CSF), under suitable conditions and for a sufficient period of time to yield alveolar-like macrophages.

6 Claims, 17 Drawing Sheets

Specification includes a Sequence Listing.

(56) References Cited

OTHER PUBLICATIONS

Litvack et al.—"Alveolar-like Stem Cell-derived Mybneg Macrophages Promote Recovery and Survival in Airway Disease", American Journal of Respiratory and Critical Care Medicine, Jan. 5, 2016 (Jan. 5, 2016) First Published online as DOI: 10.1164/rccm.201509-1838C, ISSN: 1073-449X.

Gomez Perdiguero et al.—"Development and Homeostasis of "Resident" Myeloid Cells: the case of the Microglia", GLIZ 61: 112-120, 2012 Wiley Periodicals.

Gomez Perdiguero et al.—"Myb-Independent Macrophages: A Family of Cells that Develops with Their Tissue of Residence and is involved in it Homeostasis", Cold Spring Harbor Symposia on Quantitative Biology, vol. LXXII.

Shultz et al.—"A Lineage of Myeloid Cells Independent of Myb and Hematopoietic Stem Cells", Science Apr. 6, 2021 (Apr. 6, 2012), vol. 336, No. 6077, pp. 86090, ISSN: 0033-8075.

Nakata et al.—"Granulocyte-macrophage colony-stimulating factor promotes the proliferation of human alveolar macrophages in vitro", The Journal of Immunology, vol. 147, 1266-1272, No. 4, Aug. 15, 1991.

Soucie et al.—"Lineage specific enhancers activate self-renewal genes in macrophages and embryonic stem cells", Science, Feb. 12, 216, vol. 351, No. 6274.

Imperatore et al.—"SIRTI regulates macrophage self-renewal", The EMBRO Journal, 2017, vol. 36, No. 16, p. 2353-2372.

Busch et al.—"Isolation and Long-term Cultivation of Mouse Alveolar Macrophages", Bio Protoc, Jul. 20, 2019, vol. 9, No. 14, e3302.

Haideri et al.—"Injection of embryonic stem cell derived macrophages ameliorates fibrosis in a murine model of liver Injury", Nature Partner Journals, Regenerative Medicine (2017).

Sica et al.—"Macrophage polarization in pathology", Cell. Mol. Life Sci. (2-15) 72:4111-4126.

George et al.—"Macrophage Polarization in Lung Biology and Diseases", Intech 2014.

Burke—"Macrophages as novel cellular vehicles for gene therapy", Literature Review in Expert Opinion on Biological Therapy 3(6):919-Oct. 24, 2003.

Wilson et al.—"Amelioration of emphysema in mice through lentiviral tansduction of long-lived pulmonary alveolar macrophages", Pubmed, Dec. 21, 2009.

\* cited by examiner

B

Table 1. Ligand marker profile of PSC-AM

| Marker | 1'AM | PSC-AM |
|---|---|---|
| CD80 | + | + |
| CD86 | +/- | + |
| CD206 | +/- | + |
| SIRPα | + | + |
| MHCII | - | - |
| Langerin | - | - |

A

B

SEQUENCE LISTING

<160> NUMBER OF SEQ ID NOS: 4

<210> SEQ ID NO 1
<211> LENGTH: 26
<212> TYPE: DNA
<213> ORGANISM: Artificial
<220> FEATURE:
<223> OTHER INFORMATION: primer

<400> SEQUENCE: 1
acgattcaga gctataccaa cgtcca                                      26

<210> SEQ ID NO 2
<211> LENGTH: 23
<212> TYPE: DNA

```
-continued

<213> ORGANISM: Artificial
<220> FEATURE:
<223> OTHER INFORMATION: primer

<400> SEQUENCE: 2
ctctgcagct ctgtgaagtg gtt                                              23

<210> SEQ ID NO 3
<211> LENGTH: 25
<212> TYPE: DNA
<213> ORGANISM: Artificial
<220> FEATURE:
<223> OTHER INFORMATION: primer

<400> SEQUENCE: 3
tgctcctgat gtcaacagag aacga                                            25

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
gcactatccc catgaggtct ggtc                                             24
```

MAMMALIAN ALVEOLAR MACROPHAGES DERIVED FROM PLURIPOTENT CELLS

TECHNICAL FIELD

Non-limiting embodiments disclosed herein generally relate to differentiation of cells, such as differentiation of pluripotent stem cells (PSCs) or cells derived therefrom, into alveolar-like macrophage cells.

BACKGROUND

In recent years, directed differentiation of pluripotent stem cells (PSCs) has rapidly become a major focus of regenerative medicine to help address the shortcomings of pulmonary therapeutics or transplantation. Specific efforts have focused on endoderm-derived lung epithelium tissue regeneration, while mesoderm-derived tissues in the lungs—such as non-circulating hematopoietic lineages—have received minimal attention. This oversight in pulmonary stem cell regenerative medicine has led to a failure to appropriately address the importance of the innate immune system of the lungs; particularly its most abundant population of airway cells, the alveolar macrophage (AM). This cell type is an environmentally adapted phagocytic macrophage unlike those of other tissues. Alveolar macrophages typically reside outside the epithelial barrier of the airways and are in constant contact with the external environment. It is uniquely peculiar that a cell in such a vulnerable environment exhibits an unusually long lifespan and has the capacity to self-renew within the lung apparently with little contribution from circulating monocytes. The origin of AMs has been considered in fate-tracing experiments illustrating that resident tissue macrophages, including lung macrophages, previously thought to have arisen from circulating adult monocytes, have a more primitive origin arising from early stages of embryogenesis. Furthermore, long living alveolar macrophages may differentiate from fetal monocytes during lung development, which likely arise from fetal hematopoietic stem cells (HSCs). Fetal HSCs and monocytes are distinct in transcriptional and functional profile from their respective adult counterparts, which arise shortly after birth and not during embryogenesis. Thus, the fetal HSCs retain their early developmental signatures, which distinguish them from adult circulating hematopoietic cells. Retaining this primitive signature further distinguishes AMs from the mileu of circulating or bone marrow-derived adult immune cells, which do not possess such a primitive signature and cannot fully replenish the airways with macrophages of equal robustness and longevity. This is particularly exemplified during bone marrow transplantation (BMT) when alveolar macrophages die during myeloid ablative radiation. In this circumstance, adult monocyte-derived macrophages cannot repopulate the lungs to pre-injury levels with macrophages retaining an embryonic signature and the resulting replenished airway macrophage populations display significant functional deficiencies following BMT.

Recently, it was reported that pulmonary macrophage transplantation might be a viable strategy to address a rare hereditary lung disease known as hereditary pulmonary alveolar proteinosis (herPAP). In these studies, however, adult circulating hematopoietic cells or bone-marrow derived macrophages were used as the macrophage source for transplantation and in both studies, the macrophage population was conditioned in vivo by the lung.

It would, thus, be desirable, to develop a method for generating alveolar macrophages in vitro in an effort to treat macrophage-related lung disease.

SUMMARY

In accordance with a first aspect disclosed herein, there is provided a method for generating alveolar-like macrophages from hemangioblasts. The method comprises the steps of: i) culturing the hemangioblasts in a hematopoietic-inducing medium comprising vascular endothelial growth factor (VEGF), stem cell factor (SCF) and interleukin-3 (IL-3) for a sufficient period of time to generate macrophages, and ii) culturing the macrophages in an alveolar macrophage-inducing medium comprising granulocyte macrophage colony stimulating factor (GM-CSF), and optionally comprising macrophage colony stimulating factor (M-CSF), under suitable conditions and for a sufficient period of time to yield alveolar-like macrophages.

In another aspect, a method for differentiating pluripotent stem cells into alveolar-like macrophages is provided. The method includes: i) incubating the pluripotent stem cells in a first serum-free differentiation medium to induce differentiation of the pluripotent stem cells into embryoid bodies (EBs); ii) culturing the embryoid bodies in a second differentiation medium comprising at least BMP4 and Activin-A for a period of time sufficient to generate hemangioblasts; culturing the hemangioblasts in a hematopoietic-inducing medium comprising VEGF, SCF and IL-3 for a sufficient period of time to generate macrophages, followed by culturing the macrophages in an alveolar macrophage-inducing medium comprising GM-CSF, and optionally comprising M-CSF, under suitable conditions and for a sufficient period of time to yield alveolar-like macrophages.

In another aspect, in vitro-derived alveolar-like macrophages are provided. In an embodiment of this aspect, the alveolar-like macrophages, or a precursor thereof, may be genetically modified to express a therapeutic agent.

In another aspect, in vitro-derived alveolar-like macrophages are provided which are generated from hemangioblasts in a method comprising: i) culturing the hemangioblasts in a hematopoietic-inducing medium comprising vascular endothelial growth factor (VEGF), stem cell factor (SCF) and interleukin-3 (IL-3) for a sufficient period of time to generate macrophages, and ii) culturing the macrophages in an alveolar macrophage-inducing medium comprising granulocyte macrophage colony stimulating factor (GM-CSF), and optionally comprising macrophage colony stimulating factor (M-CSF), under suitable conditions and for a sufficient period of time to yield alveolar-like macrophages.

In another aspect, alveolar-like macrophages which exhibit at least 50% greater expression of CD11b than CD11b expression in primary alveolar macrophages are provided.

In another aspect, alveolar-like macrophages which are Myb-independent are provided.

In another aspect, alveolar-like macrophages are provided which are expandable in vitro for at least about 1 month, preferably at least 2 months, more preferably at least 1-2 years, and most preferably, which are expandable in vitro for at least about 1 year.

In another aspect, alveolar-like macrophages are provided which exhibit at least about 10% greater phagocytic activity than primary alveolar macrophages.

In another aspect, alveolar-like macrophages are provided which exhibit at least a 2-fold increase in expression of at least one of the LSR or RUNx2 genes than the expression of the LSR or RUNx2 genes in primary alveolar macrophages.

In another aspect, a composition is provided comprising isolated non-naturally occurring in vitro-derived alveolar-like macrophages in a medical-grade, physiologically acceptable carrier.

In another aspect, a kit for use to generate alveolar-like macrophages from hemangioblasts in vitro is provided. The kit comprises a hematopoietic-inducing medium comprising VEGF, IL-3 and SCF in hematopoietic amounts, optionally further comprising one or more of IL-6, TPO, FLT3L and IGF-1; and an alveolar macrophage-inducing medium comprising GM-CSF, optionally further comprising one or more of M-CSF, SCF, IL-3 and IL-6.

These and other aspects and features of non-limiting embodiments will become apparent to those skilled in the art upon review of the following description of specific non-limiting embodiments in conjunction with the accompanying drawings.

BRIEF DESCRIPTION OF THE FIGURES

The non-limiting embodiments will be more fully appreciated by reference to the accompanying drawings, in which.

Figure 1:
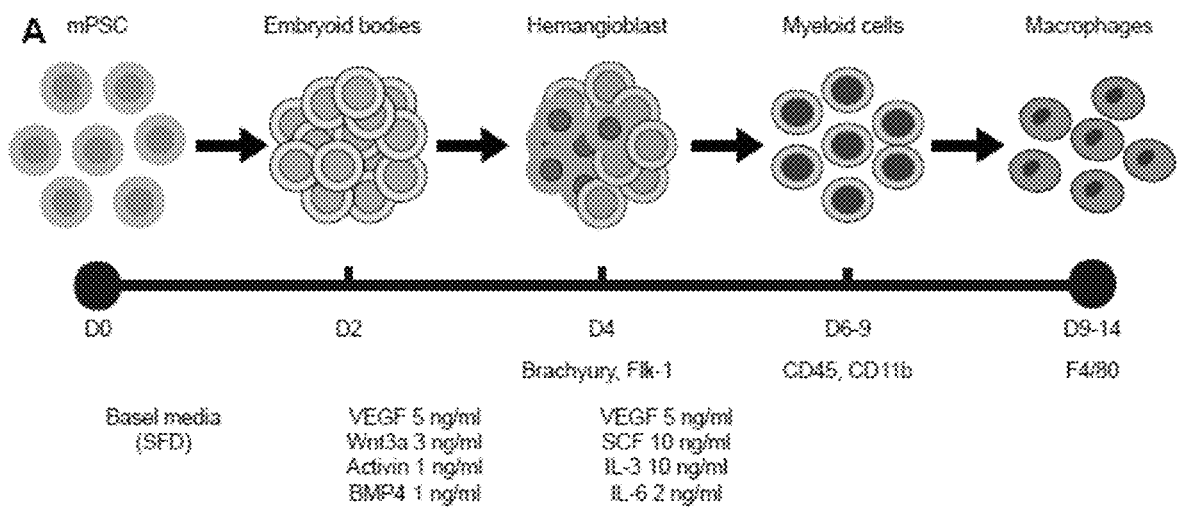
FIG. 1 depicts (A) a schematic representation of macrophage differentiation via hemangioblast hematopoiesis of murine pluripotent stem cells in serum-free, feeder-free, factor defined conditions (A) according to a non-limiting embodiment, and (B) graphically illustrates that this differentiation protocol yields myeloid macrophages as early as day 9 of differentiation with a significantly expanded population at day 14 of differentiation.
Figure 1:
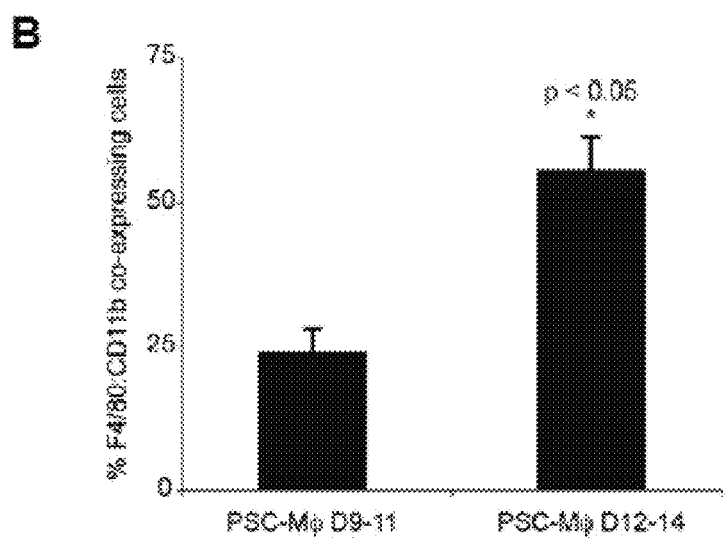

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION OF THE NON-LIMITING EMBODIMENT(S)

In a non-limiting embodiment, a method for generating alveolar-like macrophages from hemangioblasts is provided. The method comprises the steps of: i) culturing the hemangioblasts in a hematopoietic-inducing medium for a sufficient period of time to generate macrophages, and ii) culturing the macrophages in a medium comprising GM-CSF, and optionally comprising M-CSF, under suitable conditions and for a sufficient period of time to yield alveolar-like macrophages.

The present alveolar-like macrophages (ALMs) may also be referred to herein as alveolar macrophage-like cells (AMLs), pluripotent stem cell-derived alveolar macrophages (PSC-AMs) or embryonic stem cell-derived alveolar macrophages (ES-AMs).

As one of skill in the art will appreciate, hemangioblasts may be generated from pluripotent stem cells. For example, pluripotent stem cells (PSCs) are incubated in a first differentiation medium, preferably serum-free, sufficient to induce differentiation of the PSCs into embryoid bodies (EBs). The term "pluripotent stem cell" is used herein to refer to undifferentiated biological cells that can differentiate into specialized cells. In particular, PSCs are capable of differentiating into all three germ layers and becoming any cell type in an animal body. PSCs have a cell morphology characteristic of undifferentiated cells and form teratomas when introduced into an immunocompromised animal, such as a severe combined immunodeficiency (SCID) mouse. Teratomas typically contain cells or tissues characteristic of all three germ layers. Examples of PSCs include embryonic stem cells (ESCs), pluripotent adult stem cells and induced pluripotent stem cells (iPSCs). An "embryoid body" or an "EB," is an aggregate of cells derived from PSCs, which is rounded and comprises cell types derived from all three germ layers (i.e., the ectoderm, mesoderm and endoderm). Methods for generating EBs are well-known to one having ordinary skill in the art.

Media suitable for differentiation of PSCs into EBs are known to those of skill in the art, and are commercially available. For example, such media may include components such as Iscove's Modified Dulbecco's Media, Hams F-12 media, bovine serum albumin, B27 supplement without retinoic acid, transferrin, N2 supplement, ascorbic acid, L-glutamine, penicillin/streptomycin and monothioglycerol. The cells are incubated at an appropriate temperature, e.g. 37° C., generally for a time period sufficient to yield EBs in which the cells are not committed to a particular germ layer.

The method of differentiating PSCs into EBs may vary with the animal origin of the stem cell, for example, human PSCs versus non-human PSCs. In one embodiment, differentiation of human PSCs into EBs is conducted in a medium comprising one or more growth factors such as BMP4 and bFGF under hypoxic conditions (e.g. 5% 02), generally for a period of about 20-36 hours. In another embodiment, differentiation of rodent PSCs into EBs may be conducted in a medium free from growth factors at an ambient oxygen level for a period of about 45-50 hours.

The EBs are then cultured in a second differentiation medium comprising growth factors in amounts sufficient to result in differentiation of the EB cells into hemangioblasts, multipotent precursor cells that can further differentiate into either hematopoietic or endothelial cells. The second differentiation medium (preferably serum-free) may vary depending on the animal origin of the PSCs. As one of skill in the art will appreciate, differentiation may be confirmed based on cell expression of a hemangioblast mesoderm marker, such as kinase insert domain receptor (KDR) (for human cells), or Brachyury or flk-1 (fetal liver kinase-1) (for rodent cells). The medium used to differentiate EBs into hemangioblasts may include, but is not limited to, one or more mesoderm-inducing growth factors such as vascular endothelial growth factor (VEGF), Protein Wnt-3a (Wnt3a), Activin A and bone morphogenetic protein 4 (BMP4) in hematopoietic, mesoderm-inducing amounts, for example VEGF in an amount of no more than about 50 ng/ml, for example, in the range of about 5 to about 50 ng/ml; Activin A in an amount of no more than about 10 ng/ml, for example, in the range of about 0.1-10 ng/ml, and preferably 1 ng/ml; Wnt3a in an amount of up to about 5 ng/ml, for example in the range of about 1-5 ng/ml; and an amount of BMP4 of up to about 10 ng/ml, for example, in the range of about 1-10 ng/ml. In one embodiment, human EBs are incubated in a medium including 0.1-10 ng/ml Activin A for a period of time sufficient to yield hemangioblasts, e.g. about 3-5 days. In another embodiment, rodent EBs, separated into single cells, are cultured in a medium comprising VEGF, Activin A, Wnt3a and BMP4 for a period of time sufficient to yield hemangioblasts, e.g. about 45-50 hours.

The hemangioblasts are then cultured in a hematopoietic-inducing medium comprising one or more growth factors and/or cytokines, and under conditions, sufficient to promote differentiation of hemangioblasts into macrophages. The hematopoietic-inducing medium used to promote hemangioblast differentiation into macrophages may be a serum-free differentiation medium comprising a hematopoietic combination of VEGF, stem cell factor (SCF) and interleukin-3 (IL-3). The medium may optionally additionally comprise interleukin-6 (IL-6). The amounts of the growth factors in the hematopoietic-inducing medium may be in a macrophage-inducing amount, for example, an amount of VEGF of no more than about 50 ng/ml, for example, in the range of about 5 to about 50 ng/ml; an amount of IL-3 in the range of about 10-100 ng/ml; an amount of SCF in the range of about 10-100 ng/ml; and an amount of IL-6 up to about 10 ng/ml, for example, in the range of about 1-10 ng/ml. The formation of macrophages may be confirmed, for example, by staining the cells to confirm they assume macrophage morphology, by a determination that the cells express macrophage proteins such as CD40, CD45, CD11b, CD64, F4/80(mice)/EMR1 (human), lysozyme M, MAC-1/MAC-3 and CD68, or that the cells exhibit properties of macrophages such as the capacity to internalize acetylated low density lipoproteins (Ac-LDL).

Stem cell-derived macrophages obtained as described may be further conditioned to yield functional alveolar-like macrophages. As used herein, the term "alveolar-like macrophage" refers to non-naturally occurring macrophages, generated in vitro from hemangioblasts prepared from PSCs, and which express markers expressed by naturally occurring alveolar macrophages, including one or more of F4/80 (mice)/EMR1 (human), CD11c, SiglecF (mouse), CD80, CD86, CD206, CD169, CD163, CD11b, CD68, CD45 and SIRPα, and have a capacity for uptake of AcLDL. To achieve this, the PSC-derived macrophage may be cultured in an alveolar macrophage-inducing medium, e.g. a serum-free differentiation medium suitable for use with macrophages, under suitable conditions, and for a sufficient period of time, e.g. 5-8 days. The alveolar macrophage-inducing medium comprises Granulocyte-Macrophage Colony-Stimulating Factor (GM-CSF), also known as Colony Stimulating Factor 2 (CSF2), and optionally comprises Macrophage Colony-Stimulating Factor (M-CSF), also known as Colony Stimulating Factor 1 (CSF1). The alveolar macrophage-inducing medium may additionally comprise one or more of IL-3, IL-6 and SCF. The amounts of the growth factors in the alveolar macrophage-inducing medium will generally be amounts which stimulate generation of alveolar-like macrophages from myeloid macrophages, for example, an amount of GM-CSF of about 10-100 ng/ml, and optionally, an amount of M-CSF of about 10-100 ng/ml, or an amount of GM-CSF and M-CSF in a ratio ranging from about 1:10 to 10:1 GM-CSF to M-CSF. In one embodiment, GM-CSF and M-CSF are used in about a 1:1 ratio, such as about 10-50 ng/ml of GM-CSF to about 10-50 ng/ml of M-CSF, e.g. 20 ng/ml of GM-CSF to 20 ng/ml of M-CSF; IL-3 is in an amount in the range of about 10-100 ng/ml, IL-6 is in an amount in the range of about 1-50 ng/ml and SCF is in an amount in the range of about 10-100 ng/ml. The formation of alveolar-like macrophages may be confirmed minimally by expression of markers commonly expressed by alveolar macrophages such as F4/80(mice)/EMR1 (human), SiglecF (mouse), CD11c (human/mouse), CD68 (human), and uptake of AcLDL (human). Other identifying markers that may be used in addition to the foregoing include CD45, CD11b (a unique marker of alveolar-like macrophages not highly expressed by primary AMs), SIRPα, CD80, CD86 and CD206. The formation of alveolar-like macrophages may also be confirmed based on functional characteristics, such as phagocytic activity, e.g. take up apoptotic material and bacteria, and binding of the lung innate immune collectin, SP-D. Alveolar-like macrophages resulting from the method provided herein are able to attain airway residence.

In a non-limiting embodiment, a method for differentiating hemangioblasts from human PSCs into alveolar-like macrophages is provided. Hemangioblasts may be generated from human PSCs using a method comprising: i) incubating the PSCs in a serum-free differentiation medium comprising BMP4 (about 1-10 ng/mL) and basic fibroblast growth factor (bFGF) (about 1-10 ng/mL) to induce differentiation of PSCs into EBs; ii) adding Activin-A (about 0.3-1 ng/mL) to the medium and culturing the EBs for a period of time sufficient to generate hemangioblasts. To generate macrophages, the hemangioblasts are cultured in a hematopoietic-inducing medium comprising VEGF (about 5-50 ng/mL), SCF (about 10-100 ng/ml) and IL-3 (about 10-100 ng/ml) for a sufficient period of time to generate haematopoietic cells, wherein IL-6 (about 1-10 ng/mL) is optionally added during the culturing, as well as thrombopoietin (TPO) (about 10-100 ng/mL), Fms-related tyrosine kinase 3 ligand (FLT3L) (about 5-20 ng/mL) and insulin-like growth factor (IGF-1) (about 10-50 ng/mL) for a sufficient period of time to generate macrophages (e.g. for an amount of time sufficient to generate cells that detectably express CD11b, CD11c and/or CD45, and/or have a capacity to uptake AcLDL).

Macrophages generated from human PSCs may be further conditioned to yield functional alveolar-like macrophages by incubation in medium comprising GM-CSF, and optionally M-CSF (and void of growth factors such as IL-6, SCF, TPO, FLT3L and IGF-1), and culturing for a sufficient period of time to yield alveolar-like macrophages (e.g. as determined by expression of CD11b, CD11c, CD45 and/or CD68, and/or having a capacity to uptake AcLDL). The amount of each of GM-CSF, and optionally M-CSF, in the medium is in the range of about 10-100 ng/mL, in a ratio of 1:10 to 10:1, and preferably a 1:1 ratio in an amount of about 20 ng/ml each.

In one embodiment, in contrast to primary alveolar macrophages and blood-derived machrophages, the alveolar-like macrophages generated as described herein can advantageously be expanded in vitro, e.g. proliferated in cell culture for a prolonged period of time (e.g. for at least about 1 month, e.g. for 2 or more months, preferably for at least 1 year, more preferably for more than 1 year, or, most preferably, indefinitely) without senescing, losing function or dying. In this regard, expansion may be achieved in an expansion medium (with serum or serum-free) comprising M-CSF and GM-CSF in amounts ranging from about 1:10 to 10:1 M-CSF to GM-CSF. In one embodiment, expansion of alveolar-like macrophages is conducted in an expansion medium comprising a 1:1 ratio of M-CSF to GM-CSF, and in other embodiments, the amount of GM-CSF relative to M-CSF is increased during expansion, for example, GM-CSF may be doubled relative to M-CSF. Concentrations of M-CSF and GM-CSF utilized for expansion may be in the range of about 20-100 ng/ml.

In another embodiment, in contrast to primary alveolar macrophages and blood-derived macrophages, the present in vitro-derived macrophages advantageously exhibit a substantially enhanced rate of growth with a doubling rate of no more than about 5 days, no more than about 4 days, no more than about 3 days, or no more than about 2 days, e.g. from about 1-5 days, 1-4 days, 1-3 days or 1-2 days. Of note, the present macrophages exhibit a consistent enhanced rate of growth of no more than about 5 days over a prolonged period of time (e.g. for at least about 1 month, e.g. for 2 or more months, preferably for at least 1 year, more preferably for more than 1 year, or, most preferably, indefinitely) without senescing, losing function or dying. As one of skill in the art will appreciate, this growth rate occurs under circumstances that support unrestricted growth of the cells, and may fluctuate under circumstances that may hinder growth rate such as growth in reagents or vessels that may not sustain or which may impede cell growth. The enhanced rate of growth of the present macrophages was unexpected in view of the growth characteristics of primary macrophages which exhibit a comparably inferior rate of growth that is not sustained over a prolonged period of time such as 1 year, or even for shorter periods of time such as 1 or more months. Due to their unexpected growth characteristics, the present macrophages provide a viable alternative for use in cell transplantation therapy.

In one embodiment, the alveolar-like macrophages generated in vitro as described herein exhibit increased expression of one or more of CD11b, LSR and RUNx2 relative to primary alveolar macrophages.

In one embodiment, the alveolar-like macrophages generated in vitro as described herein are Myb-independent.

In one embodiment, the alveolar-like macrophages generated in vitro as described herein exhibit improved phagocytic activity relative to primary alveolar macrophages and blood- or bone marrow-derived macrophages.

In vitro-generated alveolar-like macrophages, or one or more of their precursor cell types such as PSCs, EBs, hemangioblasts or macrophages, may be genetically altered to generate alveolar-like macrophages carrying one or more genes for targeted gene correction or for targeted airway delivery of a functional therapeutic agent (such as a protein, cytokine or growth factor useful to treat a lung disease). Such genetically altered alveolar-like macrophages have advantageously been found to effectively express a desired therapeutic product without eliciting in an animal host an undesirable immune response. Examples of therapeutic agents that may be delivered via in vitro-generated genetically modified alveolar-like macrophages include, but are not limited to, anti-inflammatory agents such as IL-10, IL-1RA, IL-4, IL-11 and IL-13, antimicrobial agents such as alpha- and beta-defensins or nitric oxide synthase to optimize bacterial killing, anti-elastase agents like elafin and alpha-1 antitrypsin to reduce alveolar destruction, agents capable of dissolving mucus (e.g. deoxyribonuclease I), agents that stimulate vasodilation (e.g. prostacyclin, bradykinin, adrenaline), agents that enhance phagocytosis (e.g. calreticulin, surfactant protein A & D; mannose-binding lectin (MBL), complement proteins (e.g. C1q) and other collectins), enzymes that produce protective lipid mediators (lipoxins, resolvins, protectins, maresins), and agents that target cancer cells, such as lung cancer cells (e.g. perforin, granzyme A/B, TNF-alpha, eNOS) and attract T killer cells (e.g. IL-8, CCL2, CCL5 and CXCL10).

Genetically altered alveolar-like macrophages may be engineered to incorporate a desired nucleic acid molecule or protein using well-established biotechnological techniques. For example, a desired gene may be incorporated into a suitable expression vector using known recombinant methods, and the vector may then be introduced into target cells (alveolar-like macrophages or precursor cells) by electroporation, transfection using cationic lipid-based transfection reagents or viral-mediated transfection, e.g. lentiviral transfection. Alternatively, a therapeutic agent such as a protein or other molecule may itself be introduced into the target cells. In one embodiment, genetically altered alveolar-like macrophages may be generated by genetically altering the PSCs or intermediate cell types from which the alveolar-like macrophages are derived using the above techniques prior to induction of alveolar-like macrophage generation.

In vitro-derived genetically modified alveolar-like macrophages according to a non-limiting embodiment may be used to treat lung disease in a mammal. The terms "treat", "treating" or "treatment" are used herein to refer to methods that favorably alter a lung disease or disorder, including those that moderate, reverse, reduce the severity of, or protect against, the progression of a lung disease or disorder. For use to treat such a disease, a therapeutically effective amount of in vitro-derived alveolar-like macrophages are administered to a mammal in need of treatment. The term "therapeutically effective amount" is an amount of alveolar-like macrophages required to treat the disease that does not exceed an amount that may cause significant adverse effects to the mammal in need of treatment. Alveolar-like macrophage dosages that are therapeutically effective will vary on many factors including the nature of the condition to be treated, the mammal being treated and the dosage form utilized for administration. Appropriate dosages for use in such a treatment include dosages sufficient to result in airway residence of administered in vitro-derived alveolar-like macrophages of at least about 10%, and preferably, an airway residence of greater than 10%, for example, at least 20%, 30%, 40%, 50% or greater. In one embodiment, the dosage of in vitro-derived alveolar-like macrophages useful to treat a lung disease or disorder may be a dosage in the range of about $10^5$ to $10^8$ cells, for a sufficient period of time to achieve treatment. The treatment regimen may include daily administration of alveolar-like macrophages, or dosages administered more or less frequently, e.g. on alternate days, weekly, or multiple dosages a day. The term "about" is used herein to mean an amount that may differ somewhat from the given value, by an amount that would not be expected to significantly affect activity or outcome as appreciated by one of skill in the art, for example, a variance of from 1-10% from the given value.

Alveolar-like macrophages in accordance with a non-limiting embodiment may be formulated for therapeutic use by combination with a pharmaceutically acceptable carrier. The expression "pharmaceutically acceptable" means acceptable for use in the pharmaceutical and veterinary arts, i.e. not being unacceptably toxic or otherwise unsuitable. As one of skill in the art will appreciate, the selected carrier may vary with intended mode of administration. In one embodiment, alveolar-like macrophages may be formulated for administration by infusion or injection into a mammalian airway, e.g. intra-tracheally or intranasally, and thus, are formulated as a suspension in a medical-grade, physiologically acceptable carrier, such as an aqueous solution in sterile and pyrogen-free form, optionally buffered or made isotonic. The carrier may be a carbohydrate-containing solution (e.g. dextrose) or a saline solution comprising sodium chloride and optionally buffered. Suitable saline solutions may include varying concentrations of sodium chloride, for example, normal saline (0.9%), half-normal saline (0.45%), quarter-normal saline (0.22%), and solutions comprising greater amounts of sodium chloride (e.g. 3%-7%, or greater). Saline solutions may optionally include additional components, e.g. carbohydrates such as dextrose and the like. Examples of saline solutions including additional components, include Ringer's solution, e.g. lactated or acetated Ringer's solution, phosphate buffered saline (PBS), TRIS (hydroxymethyl) aminomethane hydroxymethyl) aminomethane)-buffered saline (TBS), Hank's balanced salt solution (HBSS), Earle's balanced solution (EBSS), standard saline citrate (SSC), HEPES-buffered saline (HBS) and Gey's balanced salt solution (GBSS).

In other non-limiting embodiments, alveolar-like macrophages may be formulated for administration by routes including, but not limited to, inhalation. In this regard, aerosol formulations may be prepared in which suitable propellant adjuvants are used. Other adjuvants may also be added to the composition regardless of how it is to be administered, for example, anti-microbial agents may be added to the composition to prevent microbial growth over prolonged storage periods.

In one embodiment, the present method advantageously provides a highly efficient growth-factor defined and extra-cellular matrix-independent in vitro differentiation protocol for the formation of macrophages from hemangioblasts derived from PSCs. Such macrophages can be further differentiated to generate alveolar-like macrophages suitable for use, e.g. for in vivo administration to mammalian lungs, to replace dysfunctional alveolar macrophages and promote survival of mammals with lung disease. The present alveolar-like macrophages exhibit improved phagocytic activity, e.g. take up apoptotic material and bacteria, as compared to primary alveolar macrophages (by at least about 10%) and bone marrow-derived macrophages (by at least about 2-fold), as well as the ability to be expanded in vitro for periods of days, months and years, a unique property of the present alveolar-like macrophages. In addition to their functional differences, the present alveolar-like macrophages exhibit molecular characteristics that differ from primary alveolar macrophages, for example, greater expression of CD11b (by at least about 50% or more, e.g. at least 60%, 70%, 80% or more as compared to CD11b expression of primary alveolar macrophages), as well as significantly increased expression of genes such as the LSR and RUNx2 (e.g. at least a 2-fold increase in expression or more, e.g. a 3-5 fold increase in expression as compared to primary alveolar macrophages).

In one embodiment, the present alveolar-like macrophages may be used to treat various macrophage-associated lung diseases. Implantation of the alveolar-like macrophages generated by the present method provides a non-pharmacological method of regenerating alveolar tissue in the treatment of genetic diseases such as adenosine deaminase (ADA)-deficiency, cystic fibrosis, hereditary pulmonary alveolar proteinosis (herPAP), and others, as well as acquired lung diseases such as chronic obstructive pulmonary disease (COPD), acute respiratory distress syndrome (ARDS), bronchopulmonary dysplasia (BPD), pulmonary fibrosis, lung cancer, radiation induced lung injury (RILI), ventilator induced lung injury (VILI), asthma, and bacterial or viral pneumonia.

In another aspect, a kit for use to generate alveolar-like macrophages from hemangioblasts in vitro is provided. The kit comprises a hematopoietic-inducing medium comprising VEGF, SCF and IL-3 in hematopoietic amounts. The medium may optionally additionally comprise IL-6, TPO, FLT3L and IGF-1. The kit also includes an alveolar macrophage-inducing medium comprising GM-CSF, optionally further comprising one or more of M-CSF, SCF, IL-3 and IL-6. Amounts of the components in the hematopoeitic-inducing medium may be as follows: an amount of VEGF of no more than about 50 ng/ml, for example, in the range of about 5 to about 50 ng/ml; an amount of IL-3 in the range of about 10-100 ng/ml; an amount of SCF in the range of about 10-100 ng/ml; and an amount of IL-6 up to about 10 ng/ml, for example, in the range of about 1-10 ng/ml, TPO (about 10-100 ng/mL), FLT3L (about 5-20 ng/mL) and IGF-1 (about 10-50 ng/mL). Amounts of components in the alveolar macrophage-inducing medium may be as follows: an amount of GM-CSF of about 10-100 ng/ml, and optionally, an amount of M-CSF of about 10-100 ng/ml, IL-3 is in an amount in the range of about 10-100 ng/ml, IL-6 is in an amount in the range of about 1-50 ng/ml and SCF is in an amount in the range of about 10-100 ng/ml.

The kit may additionally include a medium for use to prepare hemangioblasts from PSCs, including first differentiation medium for differentiation of the PSCs into EBs, optionally including one or more growth factors such as BMP4 and bFGF, and second differentiation medium for differentiation of EBs into hemangioblasts comprising one or more mesoderm-inducing growth factors such as VEGF, Wnt3a, Activin A and BMP4 in hematopoietic, mesoderm-inducing amounts. Amounts of the components of the second differentiation medium may be as follows: VEGF in an amount of no more than about 50 ng/ml, for example, in the range of about 5 to about 50 ng/ml; activin A in an amount of no more than about 10 ng/ml, for example, in the range of about 0.1-10 ng/ml; Wnt3a in an amount of up to about 5 ng/ml, for example in the range of about 1-5 ng/ml; and an amount of BMP4 of up to about 10 ng/ml, for example, in the range of about 1-10 ng/ml. The kit may additionally comprise a medium useful to expand stem cell-derived alveolar-like macrophages comprising GM-CSF and M-CSF in a ratio of 10:1 to 1:10, preferably in a ratio of about 1:1 or 2:1.

The kit may further include materials useful to conduct the present method including culture plates, welled plates, petri dishes and the like. The kit may also include instructions for conducting the present method as described herein.

Non-limiting embodiments are described by reference to the following examples which are not to be construed as limiting.

Example 1

Macrophage Differentiation Protocol

A highly efficient serum-free, feeder-free, growth-factor defined and extracellular matrix-independent in vitro differentiation protocol for pluripotent stem cell-derived macrophages was developed as follows.

Cell-Line Use and Maintenance

Pluripotent stem cells were maintained feeder-free on 0.1% gelatin coated 6-well plates in the serum-free '2i' pluripotent stem cell culture maintenance media consisting of a 1:1 ratio of Neurobasal media (Gibco, cat. #21103-049) and Hams F-12 (Gibco, cat. #11765-054); 0.5% v/v N2 supplement (Gibco, cat. #17504044); 1% v/v B27 supplement (Gibco, cat. #17502048); 0.05% w/v fraction V BSA (Gibco, cat. #15260-037); 1% v/v penicillin/streptomycin (Life Technologies, cat. #15140-122); 3 µM CHIR99021 (StemGent, cat. #04-0004); 1 µM PD0325901 (StemGent, cat. #04-0006); 1% v/v L-glutamine (Gibco, cat. #35050-061); 1000 U/mL LIF (R&D Systems, cat. #7734-LF-025/CF); 0.004% v/v monothioglycerol (Sigma, cat. #M6145-25ML). Cells were dissociated for regular passaging using TrypLE Express (Gibco, cat. #12605-028) and washed with IMDM (Gibco, cat. #12440-053). All stem cell differentiations were performed using cells of passage numbers no less than 13 to no more than 50. Embryonic stem cell (ESC) lines used in this study include FoxA2/hCD4; Bry/GFP obtained from Gordon Keller's laboratory (University Health Network, Toronto, Canada), Flk-1-eGFP (referred to as Flk-1) obtained from Janet Rossant's laboratory (The Hospital for Sick Children, Toronto, Canada) and dsRed-MST (referred to as DsRed) obtained from Andras Nagy's laboratory (Samuel Lunenfeld Research Institute, Mt. Sinai Hospital, Toronto Canada).

Cell Differentiation Culture and Media

All stem cell differentiation cultures were performed using a serum-free basal differentiation media (SFD) that consisted of 3 parts IMDM; 1 part Hams F-12 media; 0.05% w/v fraction V BSA; 1% v/v B27 supplement without retinoic acid (Gibco, cat #12587-010); 0.5% v/v N2 supplement; 100 µg/mL ascorbic acid; 1% v/v L-glutamine; 1% v/v penicillin/streptomycin; 0.004% v/v monothioglycerol (Sigma, cat. #M6145-25ML). To this SFD, growth factors and cytokines were added accordingly as described. To induce differentiation at day 0 (D0), pluripotent stem cells were adjusted to a concentration of 70,000 cells/mL and seeded into a sterile untreated low adhesion surface Petri dish. Exactly 48 hours after induction, the embryoid bodies that had developed were re-aggregated into single cells at a concentration of 75,000 cells/mL into an ultralow adhesion (ULA) cell culture plate (Corning, cat. #3471) in mesoderm-inducing media containing 5 ng/ml of VEGF, 1 ng/ml Activin A, 3 ng/ml of Wnt3a and 1 ng/ml of BMP4. On D4, the media was changed without EB re-aggregation to contain hematopoietic cocktails (10 ng/ml Il-3, 10 ng/ml SCF, 5 ng/ml VEGF and 2 ng/ml Il-6). Growth factors used in differentiation were all purchased from R&D Systems and re-constituted and stored according to the manufacturer's instructions: human VEGF (cat. #293-VE-010/CF); human Wnt3a (cat. #5036-WN-010); Activin A (cat. #338-AC-010/CF); human BMP4 (cat. #314-BP-010/CF); mouse IL-3 (cat. #403-ML-010/CF); mouse kit ligand (SCF) (cat. #455-MC-010/CF); human IL-6 (cat. #206-IL-010/CF); mouse M-CSF (cat. #416-ML-010/CF); and mouse GM-CSF (cat. #415-ML-010/CF). The CD11c macrophage populations were expanded in DMEM/F12 supplemented with 10% FBS, 1% penicillin/streptomycin, GM-CSF and M-CSF in a 2:1 ratio (usually 20 ng/ml and 10 ng/ml, respectively). All cell culture differentiations and expansions were carried out using the Corning ULA plates indicated above.

Macrophage Acetylated-LDL Uptake

Fluorescently labeled Di-acetylated-LDL (Life Technologies, cat. #L3484) was added to serum-free macrophage cell cultures for 4 hours at 37° C. 5% $CO_2$ and ambient $O_2$. Fluorescence was assessed using wide field epifluorescence microscopy.

Flow Cytometry and FACS

Cells were harvested from ULA plates. Strongly adherent cells were removed using a brief (<5 min) incubation with animal-product free TrypLE cell dissociation enzyme and combined with non-adherent cells in suspension. Cells were pelleted by centrifugation at 450×g and subjected to a second 2-3 minute incubation in TrypLE cell dissociation enzyme. Cells were washed with IMDM and resuspended in flow buffer (HBSS with 2% FBS and 1% HEPES) and passed through a 70 μm or a 40 μm filter for flow cytometry or FACS, respectively. For experiments examining the expression of macrophage ligands all cells were initially incubated with the rat anti-mouse 2.4G2 FcγR blocking antibody as per the manufacturer's recommendations (BD Bioscience, cat. #553141). Following FcγR block, fluorescently tagged antibodies for CD45-PE (BD Bioscience, cat. #553081), F4/80-APC (Biolegend, cat. #123116), CD11b-APC-Cy7 (BD Bioscience, cat. #557657), CD11c-ef450 (eBioscience, cat. #48-0114-80) and CD11c-PE (BD Bioscience, cat. #557401) and SiglecF (BD Bioscience, cat. #552126) were added to the blocked cells and incubated on ice. Cell data was acquired using the Beckman Coulter Gallios 10/3 flow cytometer and analyzed using the Kaluza flow cytometry software tool (Beckman Coulter). For cell sorting, cells were labeled as described above and sorted by The Sickkids-UHN Flow Cytometry Core Facility on a BD FACS ARIA FACS machine.

qPCR

Quantitative PCR was performed using RNA isolated from adult mouse lung tissue, mouse bone marrow and DsRED-PSC-AM. The isolation and reverse transcription was performed as described previously (Fox et al. *Stem Cells Dev.* 2014 Sep. 22 [Epub]). Primers pairs used for PU.1 detection were as follows: forward primer, 5'-ACGAT-TCAGAGCTATACCAACGTCCA-3' (SEQ ID NO: 1); reverse primer, 5'-CTCTGCAGCTCTGTGAAGTGGTT-3' (SEQ ID NO: 2). Primer pairs use for Myb detection were: forward primer, 5'-TGCTCCTGATGT-CAACAGAGAACGA-3' (SEQ ID NO: 3); reverse primer, 5'-GCACTATCCCCATGAGGTCTGGTC-3+ (SEQ ID NO: 4).

Phagocytosis Assay

Macrophages were seeded into the wells of a glass chamber slide. Primary human neutrophils, which undergo apoptosis at 37° C. within 24 hours of isolation from peripheral blood, were labeled with Vybrant DiD fluorescent dye (Invitrogen, cat. #V22887) and co-incubated with macrophages, some pre-stained with PKH26 fluorescent cell tracker (Sigma, cat. #PKH26PCL). Following the overnight co-incubation, cells were washed clean of freely floating cells (live or dead) and stained with image iT Live Lysosomal and Nuclear Labeling Kit (Invitrogen, cat. #134202), as indicated, in accordance with the manufacturer's instructions. Cells were imaged at low magnification while still alive or at higher magnification using a confocal microscope only after fixation with 4% PFA. Uptake of bacteria was performed similarly, using fluorescently tagged *Staphylococcus aureus* (Life Science Technologies, cat. #S23371). Briefly, cells were incubated at 37° C. in serum-free conditions with *S. aureus* for 90-120 minutes and washed 2-3 times with DPBS. Cells were fixed with 4% PFA and stained for membrane ligand markers accordingly. Cells were imaged by epifluorescence and/or confocal microscopy as described in the figure legends. Phagocytosis of fluorescent IgG-coated bead uptake was performed as previously described (Litvack et al. 2011. *PLoS One* 6:e17223) and the phagocytic ratio, expressed as a percentage, was determined by dividing the number of cells with beads by the total number of cells.

Primary Cell Isolation

Alveolar macrophages were obtained using previously published protocols (Litvack et al. 2011. *PLoS One* 6:e17223). Briefly, mice were sacrificed in accordance with the approved standard operating protocols of the laboratory animal services at the Hospital for Sick Children in Toronto, Ontario, Canada. The abdominal cavity of mice was opened and exsanguinated. The lungs and trachea were then revealed by continuing to open the thoracic cavity. A BD Angiocath was inserted into the exposed trachea and 1 mL of DPBS was used to inflate the lungs cyclically three times, collected and placed on ice. This was repeated 5 times for a total collection volume of 5 mL bronchoalveolar lavage (BAL) fluid per mouse. Collected fluid was centrifuged for 20 minutes at 4° C. at 400×g. The resulting supernatant represented the BAL fluid and was frozen at −20° C. The cell pellet was resuspended in sterile distilled water for 30 seconds to lyse erythrocytes and remaining cells were seeded onto a glass chamber slide or plastic cell culture plate in DMEM plus 10% v/v FBS and 1% v/v penicillin/streptomycin or analyzed by flow cytometry as described above.

Animals

Adult (6-12 weeks old) transgenic male and female mice containing the enhanced green fluorescent protein fused to the histone 2B protein (H2B-GFP) bred to multiple generations on the CD1 background strain were used in accordance with standard operating protocols of the laboratory animal services at the Hospital for Sick Children in Toronto, Ontario, Canada. Adenosine deaminase deficient (ADA) mice (FVB, 129-Ada$^{tm1Mw}$-Tg[PLADA]4118Rkmb/J) were bred under specific pathogen free (SPF) conditions and monitored daily in accordance with Laboratory Animal Services standard operating procedures. Both mouse strains were selected based on their age to ensure appropriate lung size and randomization and blinding was not necessary and therefore not used.

Clodronate Liposomes

Clodronate liposomes were purchased from Encapsula NanoScience (Nashville, Tenn.) as a registered product called Clodrosome™. The clodronate is packaged into a liposome, which upon internalization by phagocytosis releases the toxic clodronate to a macrophage and initiates macrophage apoptosis. The Clodrosome™ was administered to mice intranasally in two doses on consecutive days, first in a volume of 100 μL then in 50 μL.

In Vivo Adoptive Transfers

PSC-AMs were administered to the lungs of mice via intratracheal instillation. Briefly, mice were anesthetized with a ketamine (75 mg/kg) and xylazine (10 mg/kg) mixture. A 25 gauge BD Angiocath was inserted into the trachea of the anaesthetized mouse and $0.5\text{-}1\times10^6$ cells in 50 µL of PBS was instilled into the lungs, followed by 300 µL of air. Experiments using ADA knockout mice were performed on pups as young as postnatal day (PND) 3. Intranasal delivery of cells for the young pups was used because they are too small at this age for the intubation required for intratracheal transplantation. A separate pilot experiment was conducted to confirm recovery of DsRed-PSC-AMs cells from the airways of wild-type 3-4 day old pups that received intranasal delivery of cells. Whole litters of ADA mice that had both $ADA^{+/-}$ and $ADA^{-/-}$ pups were then used. All mice within a litter were instilled with PSC-AMs suspended in PBS via intranasal administration with $1\text{-}2\times10^5$ cells at PND3 followed by $10^6$ cells on PND4 to 7. Separate litters were used for control delivery of PBS alone using a similar delivery schedule. Following PND7, intranasal instillations with $10^6$ cells were performed on alternating days until the experimental endpoint (PND17±0.5 d). Blood gas readings were taken from arterial blood obtained from the carotid arteries and analyzed immediately on the ABL 800 Analyzer (Radiometer, Copenhagen).

Fluorescence Imaging

Fluorescence confocal microscopy was performed on a Leica CTRMIC 6000 confocal microscope with a Hamamatsu C910013 spinning disc camera (Leica Microsystems Inc.) and epifluorescence imaging was completed using a Leica DMI 3000B microscope with a Hamamatsu ORCA-HR camera (Leica Microsystems Inc.). Data was analyzed using the Velocity software suite (Perkin Elmer).

Electron Microscopy

Cells examined by electron microscopy were fixed in 2.5% (w/v) glutaraldehyde in 0.1M phosphate buffer at pH 7.4 followed by 1% osmium tetroxide. They were then dehydrated in an ascending series of acetone and embedded in Epon Araldite resin. Ultrathin sections were prepared and stained in uranyl acetate and lead citrate prior to viewing. All samples were examined on a JEOL JEM 1011 transmission electron microscope (JEOL USA, Peabody, Mass.).

Statistical Analysis

Analysis of variance was used to compare multiple means for parametric data when more than two groups were considered. When comparing multiple groups for ranked survival data the Fisher's exact test was used. When comparing two groups a t-test was performed. For all statistical tests a p<0.05 was considered statistically significant. Error bars on graphically presented data are ±SEM unless otherwise detailed in the figure legend.

Results

Macrophages Derived in Serum-Free Defined Conditions Directly from Hemangioblasts Acquire Alveolar Macrophage Characteristics when Transplanted in the Adult Lung A method was established for inducing pluripotent stem cells into early embryonic mesoderm-derived hemangioblast hematopoiesis. Pluripotent stem cells were allowed to generate embryoid bodies (EBs) for two (2) days followed by culture with vascular endothelial growth factor (VEGF), Wnt3a, Activin and BMP4 until Day 4, where co-expression of the mesoderm markers, Brachyury and Flk-1, confirmed the development of hemangioblasts. Hemangioblasts were cultured with all four soluble factors (VEGF, SCF, IL-3 and IL-6) to promote myeloid cell differentiation (FIG. 1A). Myeloid macrophages expressing both F4/80 and CD11b were detectable by flow cytometry on days 9 through 14 (D9-14) of the differentiation protocol; however, a significantly higher (55.7±5.5% vs. 24±3.8%, n=9 separate differentiations, p=0.0015) population of these cells was present by day 14 (D14) (FIG. 1B). Using flow cytometry, cells co-expressing the hematopoietic marker, CD45, and myeloid marker, CD11b, were found to be still present as a substantial population of nearly 40%±4.6% (n=12 independent differentiations), with efficiencies reaching up to 70%. Of this population, approximately 96% of these cells co-expressed the macrophage markers, F4/80 and CD11b, while a smaller proportion (~19%) of these cells also expressed the dendritic cell marker, CD11c. Fluorescence assisted cell sorting (FACS) was used to purify the macrophages based on F4/80 expression alone. Both the cells' macrophage morphology and their capacity to internalize acetylated low density lipoproteins (Ac-LDL), which is a distinguishing characteristic of macrophages within the myeloid lineage, were verified by differential stain. These data illustrate that the macrophage population achieved by the present serum-free differentiation of pluripotent stem cells are morphologically and functionally like macrophages.

Alveolar macrophages mature in response to the lung environment and express high and constant levels of the dendritic cell marker, CD11c. It was determined if the pluripotent stem cell-derived macrophages (PSC-Mp) generated could acquire and maintain the levels of CD11c expression characteristic of alveolar macrophages. F4/80-sorted PSC-Mp were labeled with PKH26 red fluorescent cell tracker and adoptively transferred into the lungs of healthy mice via the trachea to determine if the PSC-macrophages could acquire the alveolar macrophage phenotype of F4/80 and CD11c co-expression, in vivo. Total alveolar macrophage population was recovered after 1 week by performing a bronchoalveolar lavage (BAL). Flow cytometry was used to identify F4/80:CD11c co-expressing alveolar macrophages from BAL cells. These cells represented the majority of BAL cells at nearly 90% of the total cell population. From this total population, PKH26 stained cells were gated to evaluate their F4/80 and CD11c expression, and it was found that the PKH26 positive cells that at this timepoint co-expressed F4/80 and CD11c also represented more than 90% of PKH26 population despite representing less than 20% of the population prior to adoptive transfer. Thus, the PKH26 population had become indistinguishable from the resident alveolar macrophages based on co-expression of F4/80 and CD11c. These data indicated that the PSC-Mp could acquire the alveolar macrophage phenotype with characteristic F4/80:CD11c co-expression simply by residing with the appropriate in vivo conditions of the lungs.

Figure 2:
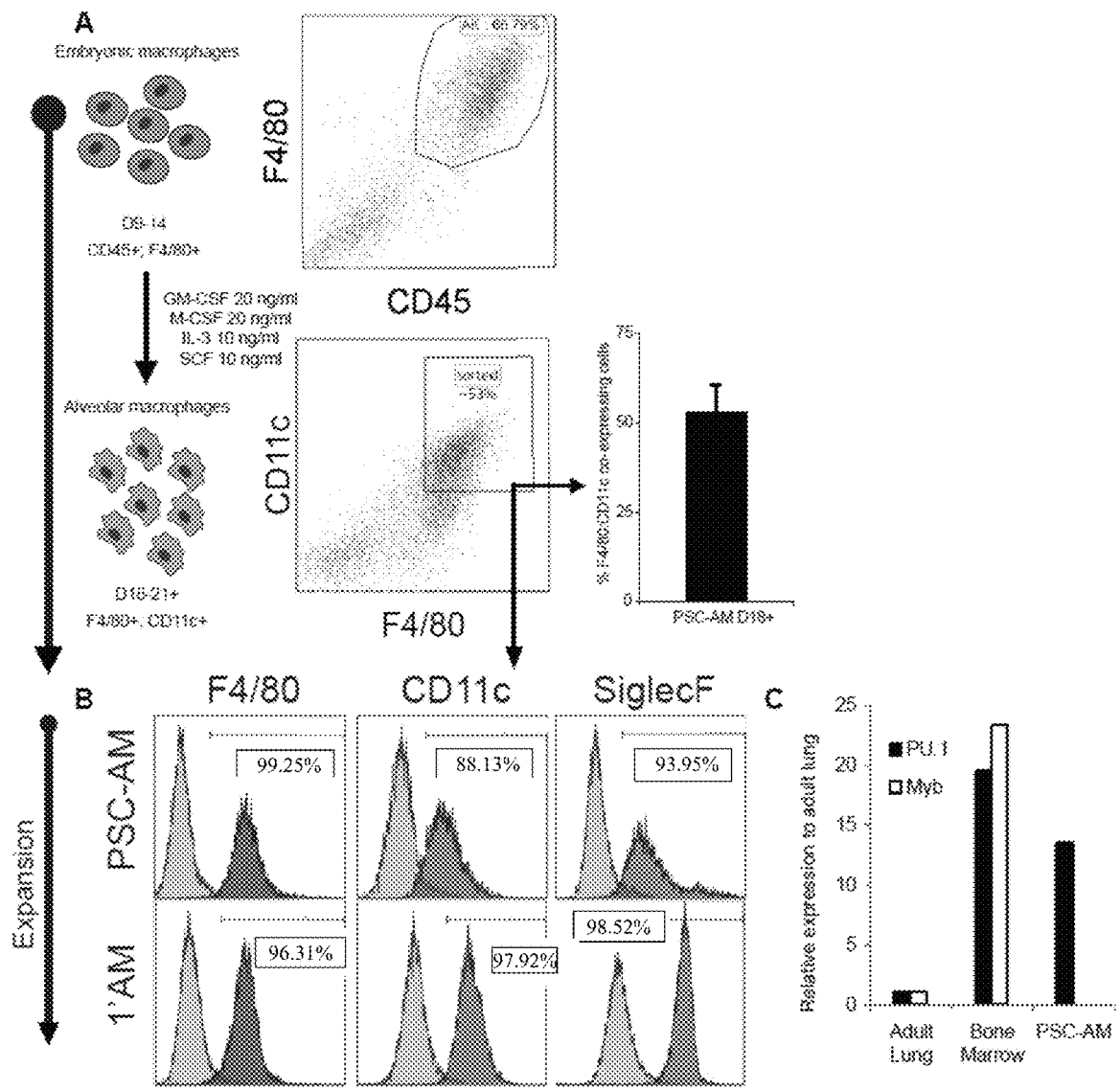
FIG. 2 depicts a schematic representation in parallel with flow cytometry of D14 PSC-Mp co-expressing CD45 and F4/80, sorted for F4/80 and cultured for 1 week with GM-CSF, M-CSF, SCF and IL-3 to promote the expression and expansion of F4/80-CD11c co-expressing macrophages (A) according to a non-limiting embodiment, graphically compares FACS results for co-expression of F4/80, SiglecF and CD11c markers of PSC-derived macrophages and primary alveolar macrophages after expansion (B) and graphically illustrates quantitative PCR of PSC-AM and bone marrow cells for macrophage transcription factor PU.1 and bone marrow myeloid transcription factor Myb (C).
Figure 3:
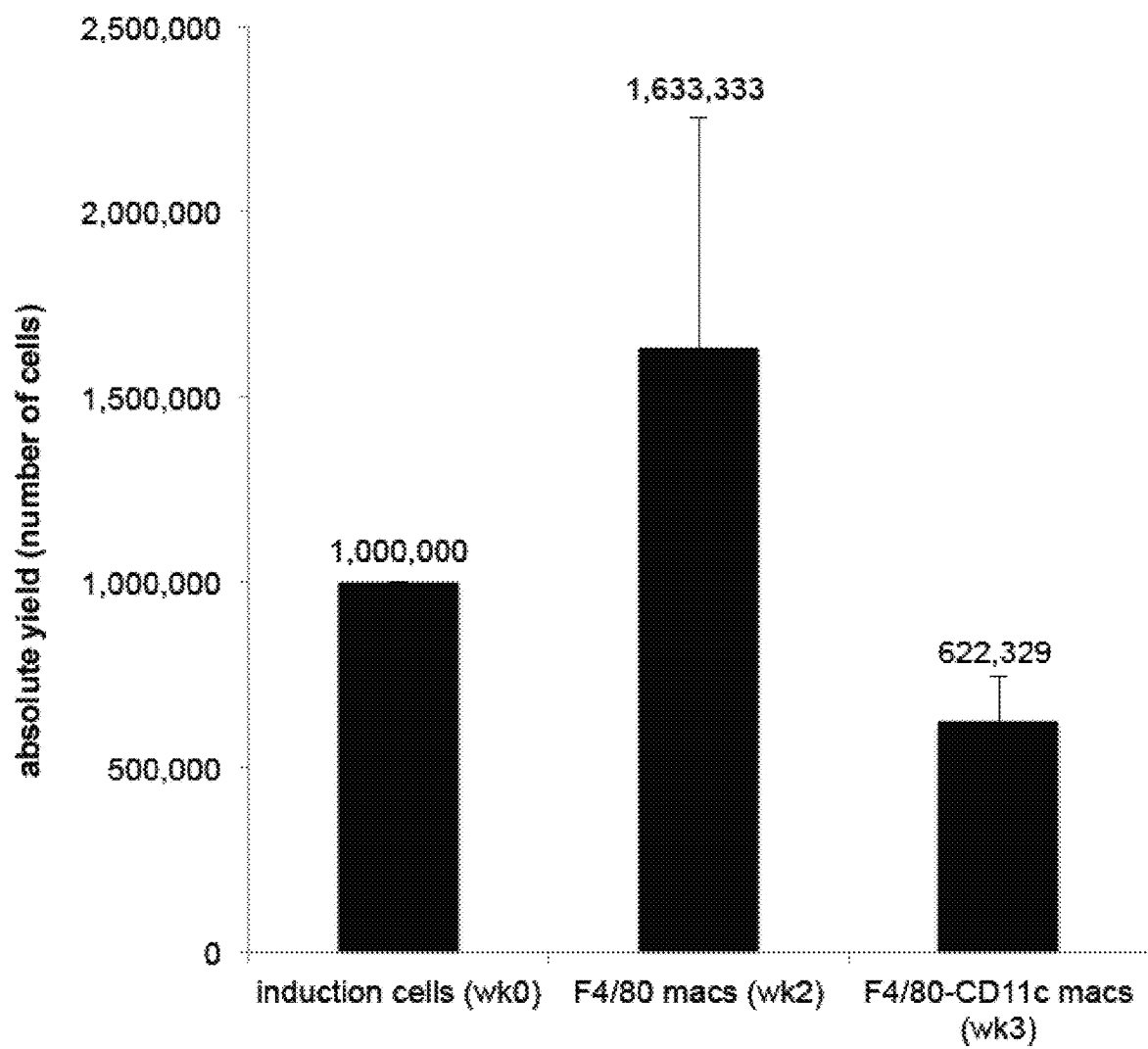
FIG. 3 graphically illustrates yield of pluripotent stem cell-derived F4/80-CD11c macrophages according to a non-limiting embodiment. Yield values are expressed as absolute cell numbers (mean±SEM, n=4 independent differentiations).
Figure 4:
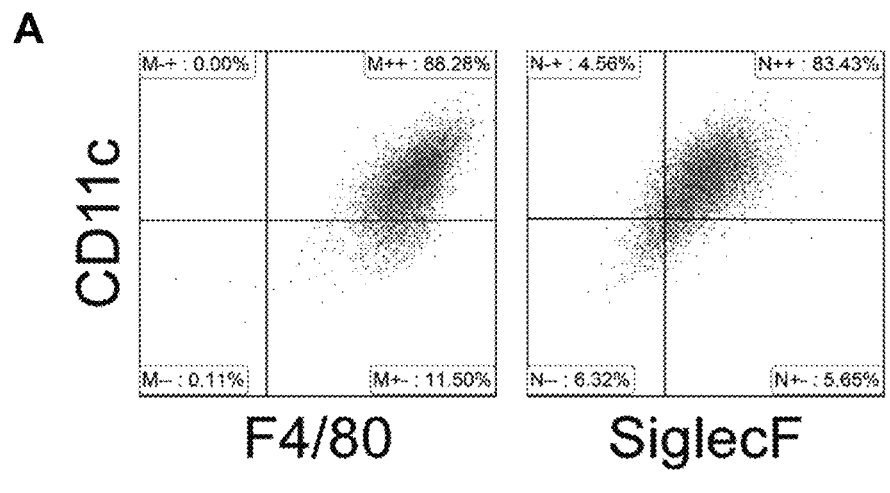
FIG. 4 illustrates that PSC-derived macrophages were confirmed to express the alveolar macrophage markers, F4/80, CD11c and SiglecF by flow cytometry following initiation of expansion (A), as well as other ligand markers (B).

In Vitro Conditioning Gives PSC-Macrophages an Alveolar Macrophage-Like Phenotype After determining that the lungs can confer an alveolar-like phenotype on the PSC-Mp, the possibility of conditioning the cells in vitro to an alveolar-like phenotype was considered. Given the role that GM-CSF plays in regulating and maintaining functional alveolar macrophages, F4/80-sorted PSC-Mp obtained on day 14 of differentiation were re-cultured with GM-CSF while using M-CSF, IL-3 and SCF to further expand the hematopoietic macrophage population over the course of the 7 day period exemplified by the in vivo adoptive transfer results presented in the previous section. The GM-CSF supplemented culture conditions helped to enhance the CD11c expression of the PSC-Mp and rendered approximately 53%±7.3% (n=9 separate differentiations) of the cells alveolar macrophage-like based again on F4/80:CD11c co-expression (FIG. 2A). Cells at this stage were noted to be Oct-4 negative and free of pluripotency (data not shown). FACS was then used to selectively acquire this population of cells that co-expressed F4/80 and CD11c, named PSC-alveolar-like macrophages (PSC-AMs). The present differentiation protocol generated a substantial yield of approximately $6 \times 10^5$ PSC-AMs for every $10^6$ uninduced cells originally cultured with growth factors during the first week of the protocol (FIG. 3). Using GM-CSF and M-CSF, the cells were expanded continuously without requiring additional sorting. The cells maintained expression of ligand markers found on primary alveolar macrophages, including F4/80, CD11c and SiglecF three weeks after their initial induction from pluripotency (FIG. 2B). Expression of SiglecF demonstrated that the expansion of the PSC-Mp did not inadvertently convert the cells to dendritic cells, which do not express this marker. Sustained co-expression of these AM markers with other markers commonly expressed on primary AMs including CD80, CD86, CD206 and SIRPα was also confirmed, and it was verified that PSC-AM do not express WWII or Langerin (FIG. 4). qPCR was used to show that PSC-AM express the macrophage transcription factor PU.1 but not Myb (FIG. 2C). This further confirmed that the macrophages generated were not Myb-dependent bone marrow-like macrophages or dendritic cells. Collectively, these data suggest that PSC-Mp can be conditioned in vitro to acquire a primary AM-like phenotype and these Myb-independent PSC-AM are phenotypically like AM and can be maintained and expanded when necessary.

Figure 5:
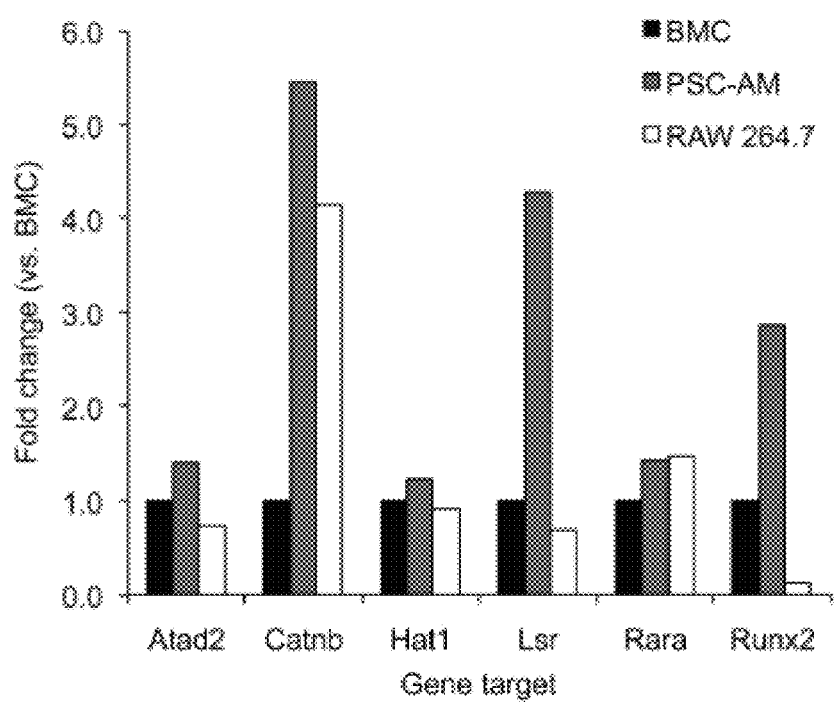
FIG. 5 graphically illustrates quantitative expression of lung macrophage targets in bone marrow cells, PSC-AMs and the RAW 264.7 macrophage-like cell line, for 6 of 21 genes known to be prominently expressed in lung macrophages. Data is presented as fold change compared to the bone marrow cells and is representative of n=3 samples.

Also using qPCR, 6 of the 21 tissue specific genes previously indicated to be highly expressed in lung macrophages were randomly selected and PSC-AMs were found to exhibit expression of all 6 genes with 3 genes highly expressed and 2 uniquely expressed, e.g. LSR (lipolysis stimulated lipoprotein receptor) gene, and RUNX2 (Runt-related transcription factor 2) gene, in comparison to bone marrow cells and RAW 264.7 cells (FIG. 5).

Figure 6:
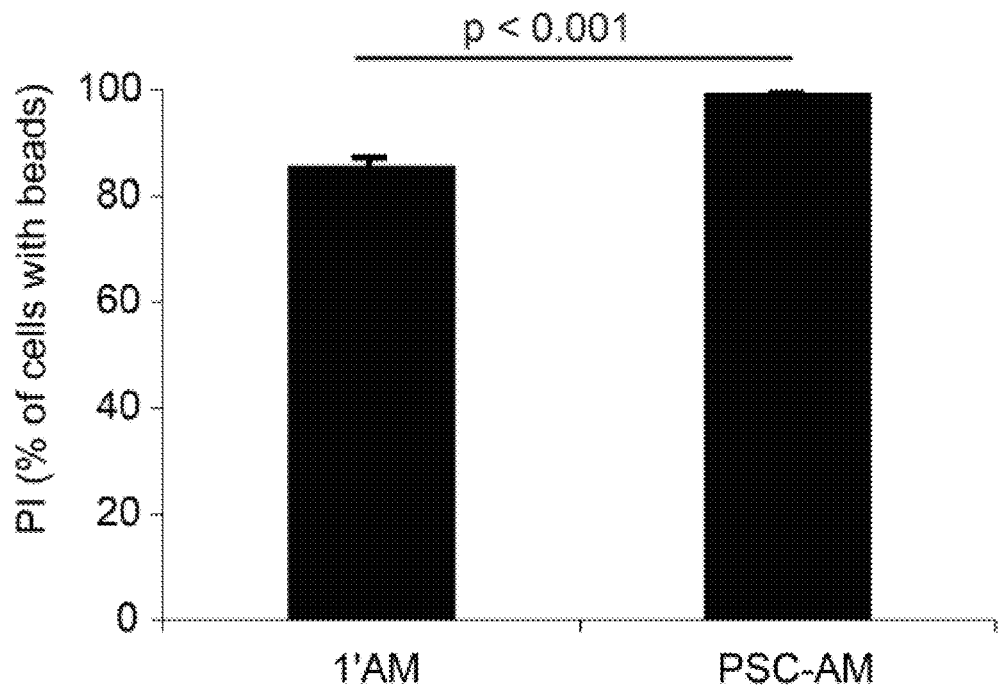
FIG. 6 graphically illustrates A) the ability of PSC-AMs and primary AMs for their ability to phagocytose fluorescent beads (PI, phagocytic index; by t-test, p<0.001, n=3, independent comparisons); B) curve fitting calculated from absolute cell numbers within a constant region of interest of BMDM and PSC-AMs cultured under identical conditions (mean±SEM of a technical replicate representative of at least 3 independent experiments); and C) Phagocytic index of PSC-AMs compared to BMDMs for uptake of IgG-coated beads (n=3 replicates, ±SEM, p<0.05 by t-test).
Figure 6:
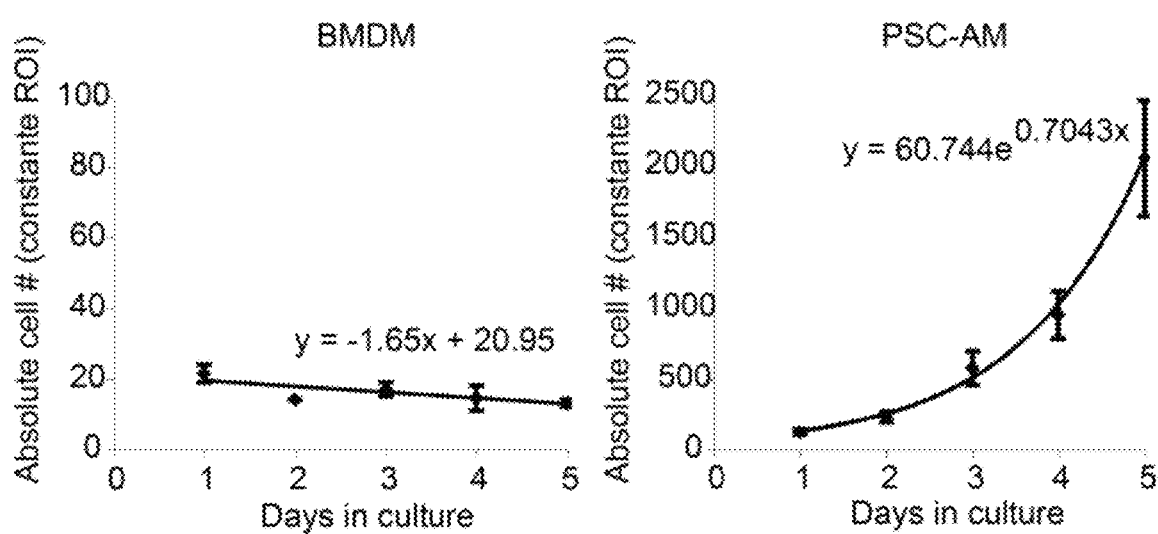
Figure 6:
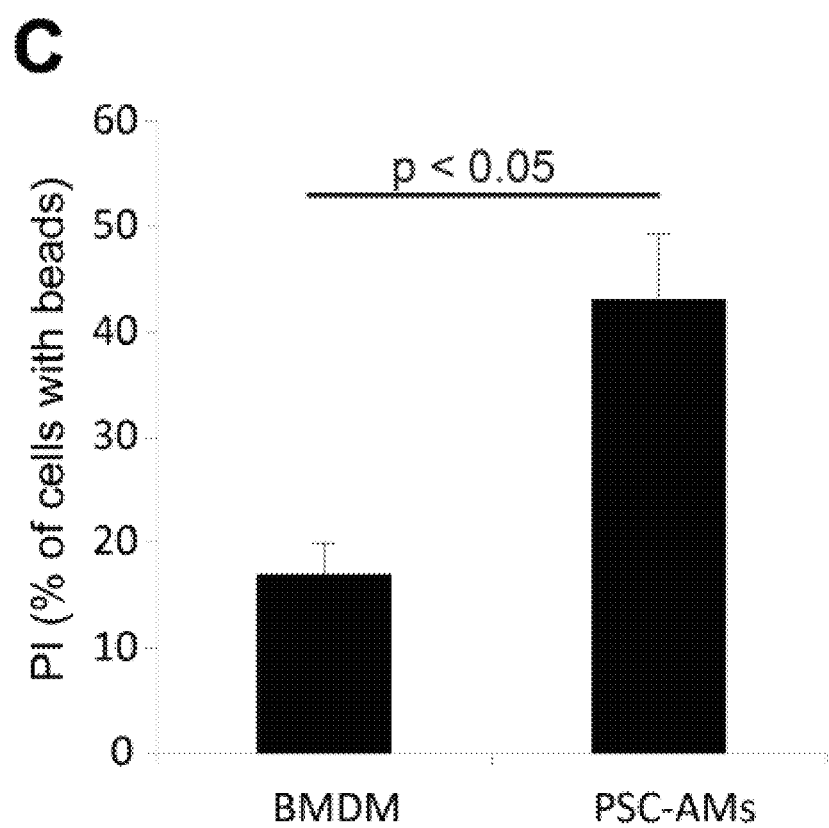
Figure 7:
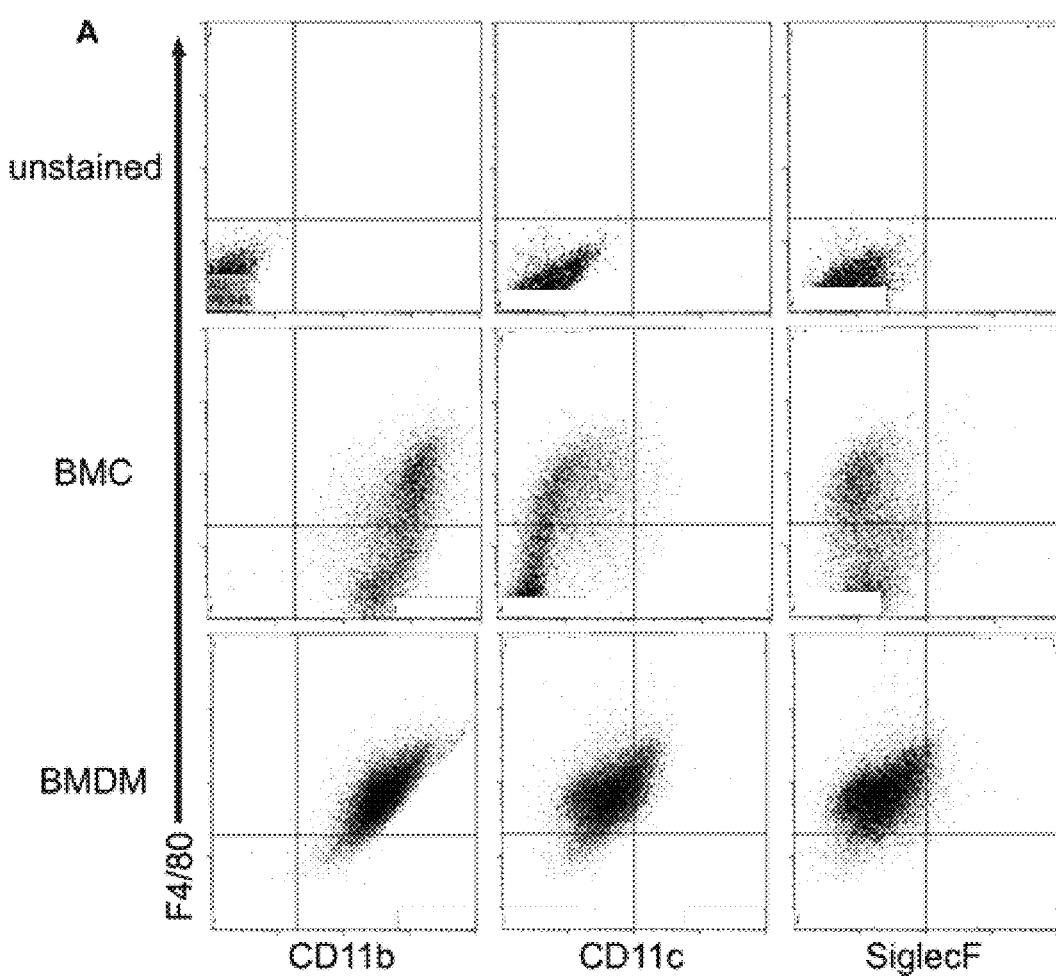
FIG. 7 illustrates ligand marker expression of alveolar macrophage markers in bone marrow cells (BMC) and bone marrow-derived macrophages (BMDM).

It was further shown that the PSC-AMs ultrastructurally resemble primary AMs and determined that the cells were highly efficient at phagocytosing IgG-coated beads (FIG. 6A), bacteria and apoptotic neutrophils, exhibiting increased phagocytosis in comparison to primary macrophages (by at least about 10%). Bone marrow cells (BMCs) were isolated from mice and the non-adherent progenitors were differentiated to BMDMs as previously described (Suzuki et al. Nature 2014; 514: 450-454) for the purpose of comparing their expansion and phagocytic potential with PSC-AMs. Only a small proportion (<20%) of the isolated BMCs and the differentiated F4/80$_+$ BMDMs co-expressed the alveolar macrophage markers CD11c and SiglecF (FIG. 7). By FACS analysis the F4/80+ population was obtained. A side-by-side comparison with PSC-AMs was performed, which determined that PSC-AMs expand at an exponential rate (curve equation: $y=60.744e_{0.7043x}$) (FIG. 6B, right), whereas BMDMs did not expand (curve equation: $y=-1.65x+20.95$) (FIG. 6B, left). The growth rate of the PSC-AMs as shown in FIG. 6B is further exemplified by the following doubling rate over time:

| PSC-AM Doubling | Days in Culture | Time to for cells to double (days) |
| --- | --- | --- |
| 1st Doubling | 1 | 1 day |
| 2nd Doubling | 2 | 1 day |
| 3rd Doubling | 2 | <1 day |
| 4th Doubling | 3 | 1 day |
| 5th Doubling | 4 | 1 day |
| 6th Doubling | 5 | 1 day |
| 7th Doubling | 5 | <1 day |
| 8th Doubling | 6 | 1 day |
| 9th Doubling | 6 | <1 day |
| 10th Doubling | 7 | 1 day |

It was also found that PSC-AMs were nearly three times more efficient at phagocytosing IgG-coated beads than were BMDMs (BMDM, 16.98±2.97% vs. PSC-AMs, 43.18±6.18, n=3 independent replicates, p=0.019) (FIG. 6C). With respect to surface ligand macrophage markers for mouse primary alveolar macrophages as compared to mouse PSC-AMs, mouse primary AMs express F4/80 and CD11c, but only a small proportion express CD11b (about 15-20%), whereas PSC-AMs express all ligand markers, including CD11b (about 80%).

PSC-AM are Functionally Similar to Primary AM

Figure 8:
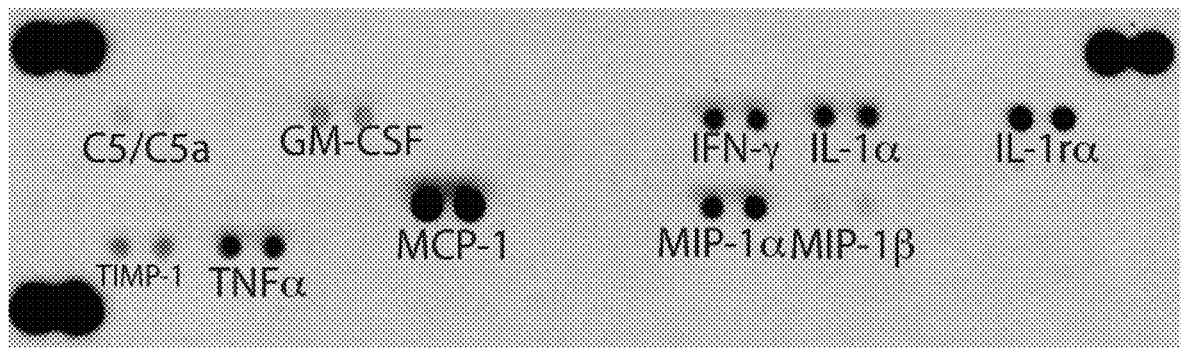
FIG. 8 illustrates a ligand plot (A) and graph (B) confirming that the basal polarization status of PSC-AMs generated using the present method exhibit properties of classically activated M1 macrophages.
Figure 8:
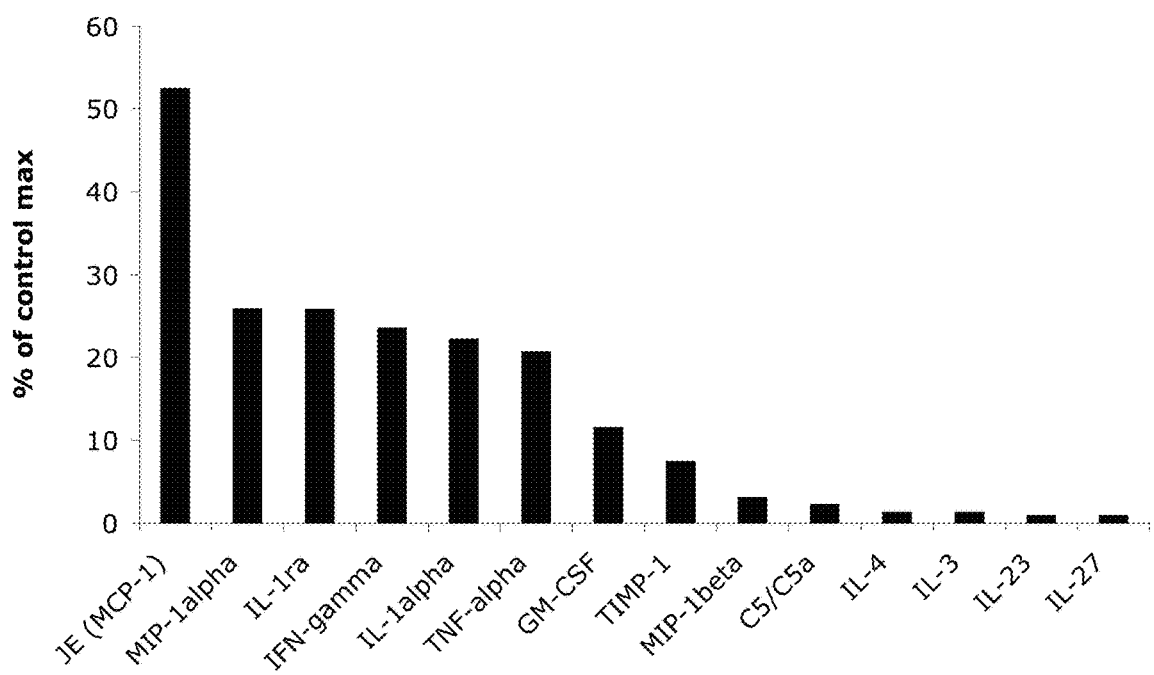

Upon confirming that the cell surface ligands of the PSC-AM are similar to primary AMs, a series of in vitro experiments were conducted to evaluate the functional characteristics of PSC-AMs. Using transmission electron microscopy PSC-AM were compared to primary AM. Large organelles resembling phagosomes were identified in both primary and PSC-AMs. Thus, the PSC-AM were considered to be functional phagocytes like primary AM. A bead uptake analysis was then conducted by incubating PKH26-labelled (red) PSC-AMs with fluorescent (green) IgG-coated beads and the PSC-AM were found to be more efficient in phagocytic uptake of the antibody-coated beads than primary AM. To further characterize the PSC-AM, a red fluorescent lysotracker was used to identify lyosomes in the PSC-AM and primary AMs, which were similarly abundant in both cell types. These primary and PSC-AMs were co-incubated with fluorescently labelled apoptotic neutrophils to confirm that PSC-AM take up apoptotic material just like primary AM. In many infectious lung diseases, alveolar macrophages are responsible for clearing bacteria from the airways. To confirm that PSC-AM internalise bacteria, PSC-AM were co-incubated with green fluorescent bacteria. It was confirmed in vitro by examination under fluorescent widefield and confocal microscopy and transmission electron microscopy that these cells readily phagocytose bacteria. The basal polarization status of PSC-AMs was evaluated and it was found that they share properties of classically activated M1 macrophages (FIG. 8). Taken together these data illustrate that PSC-AMs share morphological and in vitro functional similarities to primary alveolar macrophages.

PSC-AMs Remain in Healthy Airways after Delivery and are Functional Phagocytes During Acute Lung Injury After establishing that PSC-AM are characteristically and functionally like AM in vitro, it was determined if these cells could function in the lungs in vivo. Using the protocol described above, PSC-AMs were produced and expanded derived from an embryonic stem cell-line that constitutively expresses the DsRed fluorophore (dsRed-MST) so cells could be tracked without concern for fluorescent depletion over time. Prior to pulmonary instillation, it was confirmed that the DsRed-PSC-AMs had pulmonary innate immune potential by detecting the binding of the lung innate immune collectin, SP-D, in a population of the cells. Cells were stained with primary antibodies targeting human SP-D and an ALEXA-488 secondary fluorescent antibody to detect SP-D binding. A population of DsRED-PSC-AMs displayed the typical punctate binding characteristic of SP-D binding to alveolar macrophages. The expanded DsRed-PSC-AMs were tracheally transferred to the lungs of healthy mice to determine if the cells would take residence in the airways. After 1 week, the animals were sacrificed to perform bronchoalveolar lavages (BAL) on the mice and harvest their spleens. $DsRed^+$ cells were recovered directly from the airways but not from the spleen indicating that the cells remained in the airways. To reliably distinguish the DsRed-PSC-AMs from the resident AM population, H2B-eGFP mice were used, which express eGFP linked to histone in all nucleated cells. Using flow cytometry, the cells were examined from BAL of mice 2 h, 2 d, 2 wks, and 4 wks after airway delivery to determine if any DsRed cells remained throughout the surveyed timepoints. Constant DsRed population was detected that was distinctively separate from the host-derived GFP fluorescent cells. The total recovered BAL cell population was stained with fluorescent antibodies targeted to F4/80 and CD11c and the cells were gated based on DsRed and GFP. This gating strategy revealed that the majority of the DsRed cells transplanted to the airways continued to retain their AM expression characteristics of F4/80 and CD11c throughout the time points surveyed, with approximately 70% co-expression at 2 h, 85% at 2 d and 95% both at 2 and 4 wks. Resident AM co-expressing F4/80 and CD11c represented the majority of BAL cells recovered from the airways over the four time points surveyed. These data demonstrate that PSC-AMs are able to attain airways residence and retain AM ligand markers while remaining present for extended durations in the airways.

Figure 9:
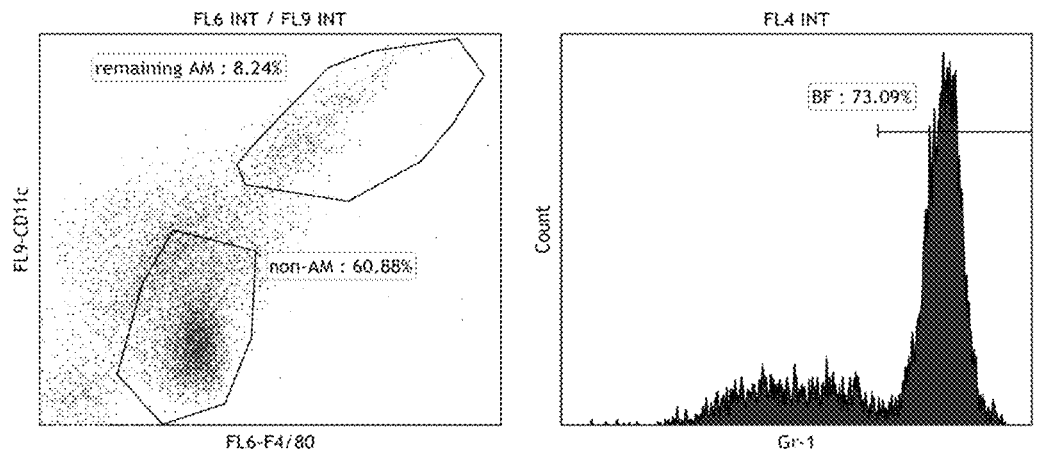
FIG. 9 illustrates that intranasal clodronate liposome treatment depletes macrophages and results in an influx of Gr-1 expressing neutrophils (A/B).
Figure 9:
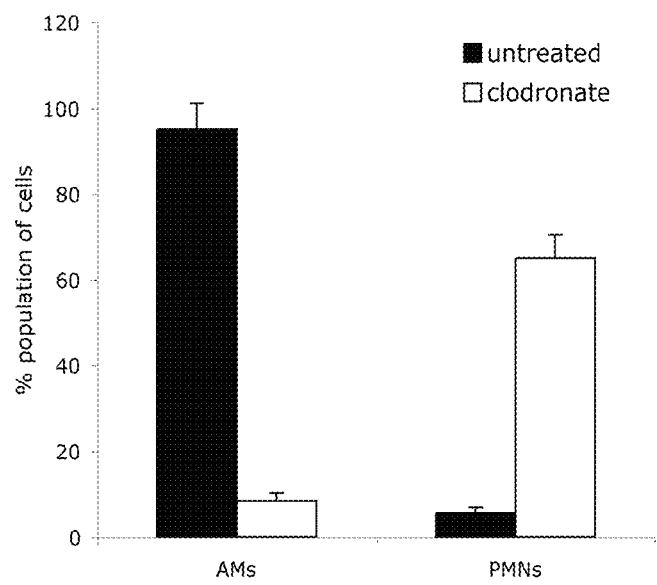

After observing that PSC-AMs can reside in the airways of healthy mice without an obvious compromising immune response, it was then determined how these cells would fare in a state of acute lung injury. Clodronate liposomes that are phagocytosed by macrophages to induce macrophage cell death have been used in a number of models to deplete airway macrophages. Thus, AM macrophages were partially depleted by delivering clodronate liposomes intranasally to healthy GFP-expressing adult mice. This depletion caused an influx of Gr-1 expressing neutrophils (FIG. 9) to the airways within 48 h of clodronate delivery, similar to that observed during acute lung injury. DsRed-PSC-AMs were subsequently delivered to the clodronate-treated airways of GFP mice to evaluate the functional properties of the PSC-AMs in vivo and determine if the PSC-AMs could perform phagocytosis in vivo. DsRed-PSC-AMs were delivered intratracheally to clodronate-treated mice four (4) days after the clodronate liposome treatment to reduce the risk that residual clodronate in the airways would affect the PSC-AMs upon delivery. BAL cells were then obtained from these clodronate-treated mice and evaluated by flow cytometry. DsRed-PSC-AMs cells remained in the injured lungs for 2 hours, 2 days and 6 days post instillation, which constituted up to 10 days following the initial clodronate injury. Moreover, approximately 90% of the DsRed population of cells retained their F4/80:CD11c co-expression characteristics during the lung injury, whereas the total population of $GFP^+$ BAL cells was comprised only partially of $F4/80^+:CD11c^+$ macrophages. Furthermore, 2 h after delivery of the DsRed-PSC-AMs to the injured lungs, host-derived material (containing GFP) was detectable within the DsRed-PSC-AMs that were recovered from the airways of clodronate-treated mice. Phagocytosis of host-derived GFP material continued until the endpoint, i.e. 6 days after DsRed-PSC-AM delivery. Additionally, differential staining of the BAL cells at each outlined timepoint was consistent with lung injury resolution.

In a separate and distinct experiment, DsRed-PSC-AM instillation into the lungs of healthy mice was preceded by airway delivery of fluorescent bacteria (*S. aureus*). Within 2 hours the DsRed-PSC-AMs had performed phagocyotosis in vivo and engulfed the bacterial particles. These data illustrate that PSC-AMs persist in healthy lungs and can remain in the lungs and be functionally active during and subsequent to injury resolution in vivo.

Repeated Intranasal Delivery of PSC-AMs to $ADA^{-/-}$ Pups Promotes their Survival, Gas Exchange and Airway Regeneration That PSC-AMs remain functional in healthy, injured and injury-resolving lungs indicates that these cells could be used for therapeutic interventions in a variety of acquired or inherited chronic lung diseases. The purine metabolic abnormality adenosine deaminase deficiency (ADA) has been characterized in transgenic mice lacking the gene. These $ADA^{-/-}$ animals develop a variety of pulmonary abnormalities shortly after birth, including compromised alveologenesis, fibrosis, inflammation, alveolar proteinosis and airway obstruction. Recent reports indicate that these animals die of respiratory failure within 18-21 days of birth and that their alveolar macrophages are non-functional, foamy and dying by apoptosis. The PSC-AM were tested in this ADA−/− model to determine if they could mitigate the pathophysiological effects of this multifaceted lung disease.

Figure 11:
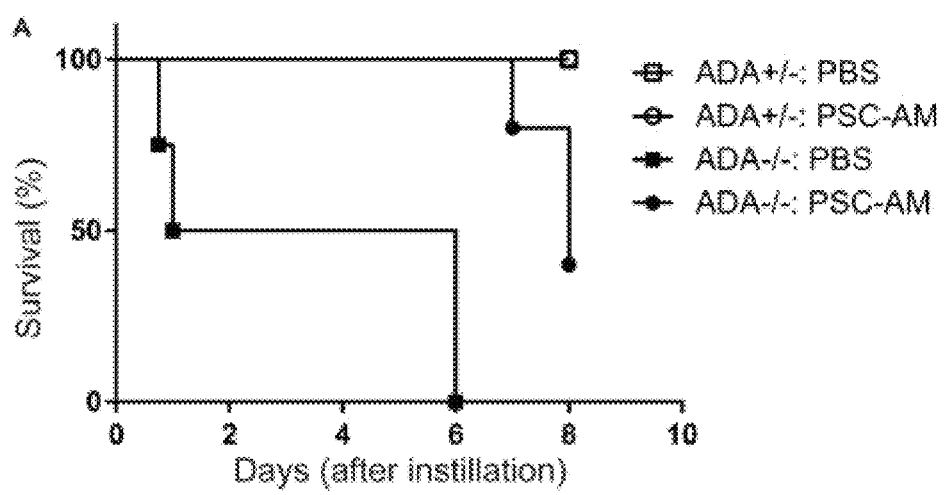
FIG. 11 graphically illustrates survival of $ADA^{-/-}$ animals after receiving one direct intratracheal instillation of PSC-AM (significance of Kaplan-Meir survival curves determined by Log-rank (Mantel-Cox), p<0.0001, n≥4 per group).

Like their human counterparts, ADA−/− mice can be saved with continuous administration of PEG-ADA. To test the effectiveness of a single intratracheal dose of PSC-AMs, 4 week old $ADA^{-/-}$ mice were used that were allowed to survive by weekly administration of PEG-ADA. Prior to administration of PSC-AMs, PEG-ADA was discontinued and ~$10^6$PSC-AMs in PBS or PBS vehicle alone was delivered directly to the airways of $ADA^{+/-}$ or $ADA^{-/-}$ mice (n≥4 per group) and the survival of animals was monitored. The $ADA^{-/-}$ mice receiving PSC-AM appeared healthy, vital and remained alive for at least 1 week after the single intrapulmonary dose of PSC-AMs, while half of the $ADA^{-/-}$ mice receiving only PBS were deceased by 48 hours. Within 6 days all PBS-treated $ADA^{-/-}$ animals were either deceased or required sacrifice. This difference in survival rates between the PSC-AM- and PBS-treated groups was statistically significant (log-rank, p<0.0001) (FIG. 11).

Figure 10:
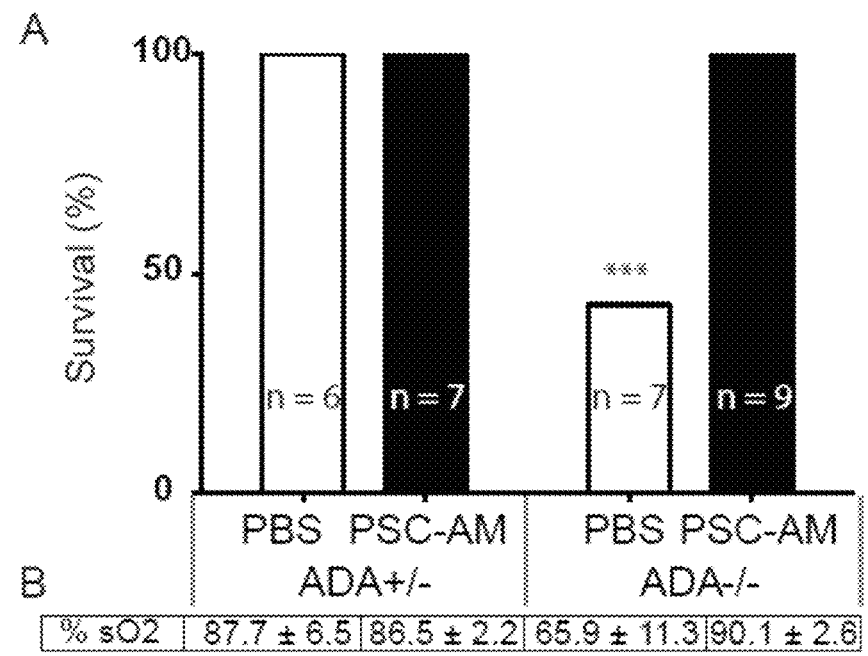
FIG. 10 graphically illustrates that PSC-AMs promote survival, recovery and patchy regeneration of airways in ADA-k/o mice. (A-B) PSC-AMs or PBS (vehicle) was administered by multiple intranasal instillations to $ADA^{-/-}$ mice and their heterozygous ($ADA^{+/-}$) littermates from as early as PND3 until the defined endpoint of PND17±0.5. (A) Survival of the animals at the defined endpoint was compared using live/dead scoring (live=1, dead=0). (B) The mean arterial blood oxygen saturation was recorded for surviving animals. (C) Scoring of Periodic acid-Schiff (PAS) positive material in the airways of PSC-AM or vehicle (PBS)-treated heterozygote and ADA-k/o mice.
Figure 10:
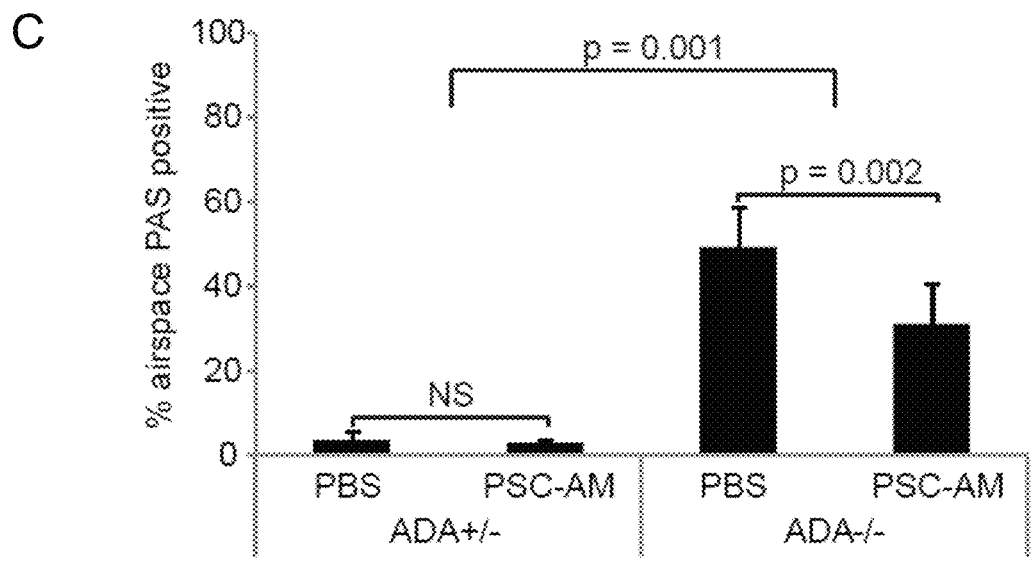

PSC-AMs were intranasally delivered into the airways of 3-4 day old ADA+/− and $ADA^{-/-}$ pups until day 15 as described in the methods section (the first delivery consisted of ~$5\times10^5$ cells and each subsequent delivery consisted of $1\times10^6$ cells). The animals were sacrificed at the defined endpoint of PND17±0.5, purposefully preceding the reported mortality limitation of $ADA^{-/-}$ mice. It was found that intranasal delivery of PSC-AM or PBS to heterozygotic ($ADA^{+/-}$) animals had no effect (neither negative nor positive) on survival as both groups of animals survived to the defined endpoint of PND17±0.5 (FIG. 10A, two bars on left). When delivered PBS to the airways of ADA$^{-/-}$ mice most of the animals died and only 43% (3 of 7) animals survived (95% CI, p=0.0002) to the defined endpoint; however, all ADA$^{-/-}$ mice (100%, 9 of 9) treated with PSC-AM survived to the same endpoint (FIG. 8A, two bars on right). Interestingly, in a separate pilot experiment, intranasal delivery to ADA$^{-/-}$ mice starting at PND12 resulted in the mice dying (data not shown). Upon sacrifice of surviving animals, arterial blood was obtained directly from the carotid artery to evaluate mean arterial blood saturated oxygen levels. ADA$^{+/-}$ littermates treated and untreated with PSC-AM both displayed oxygen saturation levels of 87.7%±6.5% and 86.6±2.2%, respectively (FIG. 10B left boxes). The saturated blood oxygen levels in PBS-treated ADA$^{-/-}$ mice was 65.9%±1.3%; yet PSC-AM-treated ADA$^{-/-}$ mice displayed blood oxygen saturation levels of 90.1%±2.6%, comparable to that of their heterozygotic littermates (FIG. 10B, right boxes).

The airways of lungs of the sacrificed animals from both the PSC-AM and PBS treated groups of heterozygotic and ADA$^{-/-}$ mice were examined by electon microscopy, and it was found that the alveoli of untreated ADA$^{-/-}$ mice were filled with a fibrillar mucous-like substance and populated with many nonfunctional macrophages. In stark contrast, ADA$^{-/-}$ mice treated with PSC-AM displayed alveolar space with reduced mucous substance. Periodic acid-Schiff (PAS) stain of lung samples from all 4 groups of mice was performed. The percentage of PAS-positive airspace was significantly different amongst both ADA$^{+/-}$ and ADA$^{-/-}$ mice (p=0.001); however, within the ADA$^{-/-}$ group alone mice treated with PSC-AM had a significantly (p=0.002) lower percentage of their airspace stain positive for PAS (31%±5.3%) compared to the PBS-treated mice (49.3%±9.3%) (FIG. 10C). Upon further examination of the airways by transmission electron microscopy, it was observed that ADA$^{-/-}$ mice treated with PSC-AM displayed focal areas of regeneration of alveolar tissue and cells. In PBS-treated ADA$^{-/-}$ mice, the alveolar basement membranes were degenerating and damaged, whereas in the treatment group, ADA$^{-/-}$ mice receiving PSC-AM displayed intact alveolar basement membranes. Furthermore, it was noted that alveolar type II pneumocytes in PBS-treated ADA$^{-/-}$ mice were dying but when the mice were treated with PSC-AM, many of the pneumocytes had recovered. Taken together, these clear differences between PSC-AM-treated and untreated ADA$^{-/-}$ mice in alveolar structure, gas exchange and animal survival indicates that PSC-AM are functionally active during the multifaceted chronic lung disease characterized in ADA$^{-/-}$ newborn mice and contribute positively to the recovery of respiratory physiology and function. Finally, a separate pathology follow-up of mice at four (4) and six (6) months after receiving PSC-AMs demonstrated that the mice were clear from any abnormal tissue growth or teratoma formation. These data illustrate that PSC-AMs persist in healthy lungs and are functionally active during and subsequent to injury resolution in vivo with no significant pathological consequences.

Figure 12:
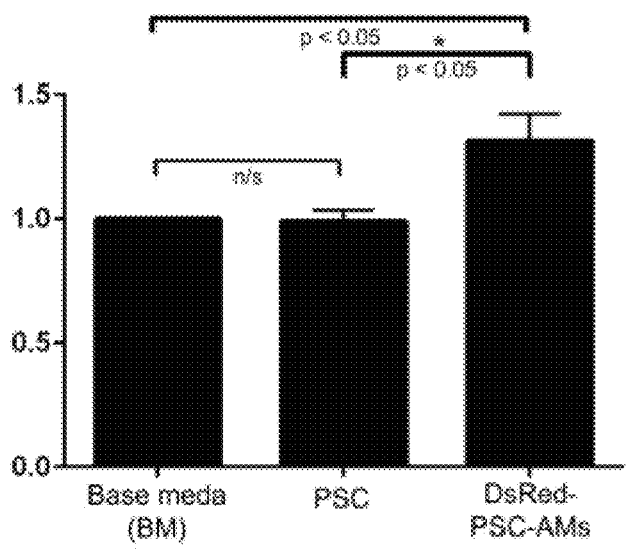
FIG. 12 graphically compares epithelial cell migration normalized to BM treatment of PSC and PSC-AMs (n≥3 replicates, p<0.05 by ANOVA).

The epithelial repair observed in ADA$^{-/-}$ mice treated with PSC-AMs led to the hypothesis that the PSC-AMs could actually enhance epithelial tissue repair. To test this, a series of migration scratch assays were performed on confluent primary fetal rat lung epithelial cells harvested as previously described (Kroon et al. Am J Physiol Lung Cell Mol Physiol 2013; 305: L795-804), in the presence of PSCs, PSC-AMs or no additional cells. The PSC-AMs, but not PSCs, were able to significantly increase (p<0.05) the migration rate of the injured epithelial cells in comparison to base media (BM) and PSC alone (FIG. 12).

Example 2

Figure 13:
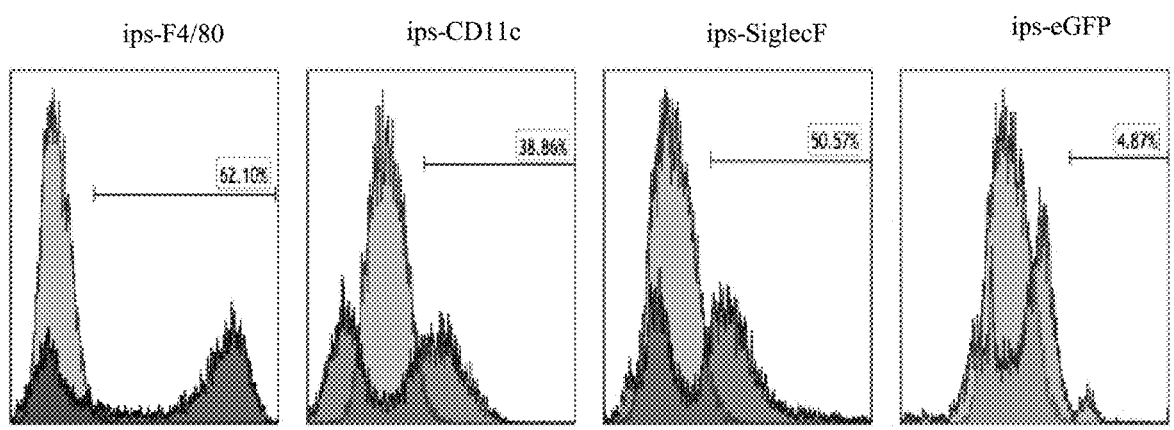
FIG. 13 illustrates murine induced pluripotent cells comprising a GFP marker of pluripotency that were differentiated into macrophages, as confirmed by expression of F4/80 and the alveolar macrophage markers CD11c and SiglecF, and the macrophages displayed negligible GFP expression.

Murine-induced pluripotent cells (iPS cell-line EOS-29, obtained from Dr. James Ellis, Hospital for Sick Children) were also used to generate alveolar-like macrophages. Using the identical protocol described in Example 1, murine induced pluripotent cells that express GFP only when pluripotency is induced, were differentiated into macrophages and sorted on Day 14 for F4/80 expression, while excluding any GFP-positive cells. One week later on Day 22 cells were confirmed to express F4/80 and the alveolar macrophage markers, CD11c and SiglecF, while displaying negligible GFP expression (FIG. 13).

Example 3

Human pluripotent stem cells (CA1, H1 and H1-GFP cells) were differentiated into CD11c macrophages. Using a serum-free factor-defined differentiation protocol similar to that described in Example 1, human pluripotent cells were differentiated to mesoderm through embryoid body formation using BMP4 and specified haemangioblast and blood precursor generation with low concentrations of activin followed by haematopoietic expansion with IL-3 and SCF culminating in macrophage colony growth with M-CSF and CD11c induction and maintenance with GM-CSF (FIG. 14A).

More specifically, human pluripotent stem cells growing in 5% O2 were harvested on day 0 (D0) from serum-free, feeder-free or feeder-dependent conditions, by a brief 5 minute incubation with TrypLE (Life Technologies) followed by scraping or feeder depletion. Scraped or feeder-depleted cell clusters were resuspended in StemPro 34 hematopoeitic media (Life Technologies) supplemented with 10 ng/ml of BMP4 and incubated overnight in an Ultra Low Adhesion (ULA) (Corning) six well culture plate in 5% O2. This procedure was distinct from mouse differentiation since mouse cells remain growth factor free for up to 48 hours after EB induction begins and all of the mouse differentiations are completed with ambient oxygen levels. On D1 (i.e., the next day following harvest), 5 ng/ml of bFGF was added to the culture. The addition of FGF2 is specific to human differentiation and not used with mouse cells. On day 2 (D2) a very low concentration of Activin A (ranging from 0.1-10 ng/ml) was added to the floating culture of embryoid bodies and remained in the culture until day 4 (D4). On D4 (where KDR expression is expected), Activin and BMP4 were removed and VEGF (10 ng/ml) and IL-6 (10 ng/ml) were added. The addition of VEGF at this timepoint and this concentration is specific to the human differentiation process (in mice VEGF is added at D2 at a concentration of 5 ng/ml). On D4-D6, SCF and IL-3 were added to the floating EBs at a concentration of 50 ng/ml (ranging from 10-100 ng/ml). The addition of SCF at this timepoint is specific to human differentiation; whereas SCF is added to differentiating mouse cells on D4 at a concentration of 10 ng/ml. On D8, VEGF and bFGF are removed from the floating EBs. TPO (50 ng/ml), FLT3L (10 ng/ml) and IGF-1 (25 ng/ml) were added to the cultured EBs and the incubations then continued at ambient oxygen levels. Cells continued to grow under these conditions until D14. GM-CSF (50 ng/ml) and M-CSF (50 ng/ml) were then added to the cells (which included a substantial macrophage population), or GM-CSF alone was added. The concentrations of GM-CSF and M-CSF were higher for human culture than the concentrations used for mouse cells. At D22, alveolar-like macrophages were identified. M-CSF was added (if not already present) and GM-CSF concentration was adjusted to twice that of M-CSF (i.e. GM-CSF, 100 ng/ml and M-CSF, 50 ng/ml) and all other growth factors were removed from culture for expansion. Similar to the mouse differentiation, macrophage colonies continued to expand under the control of M-CSF and GM-CSF beyond D35.

Figure 14:
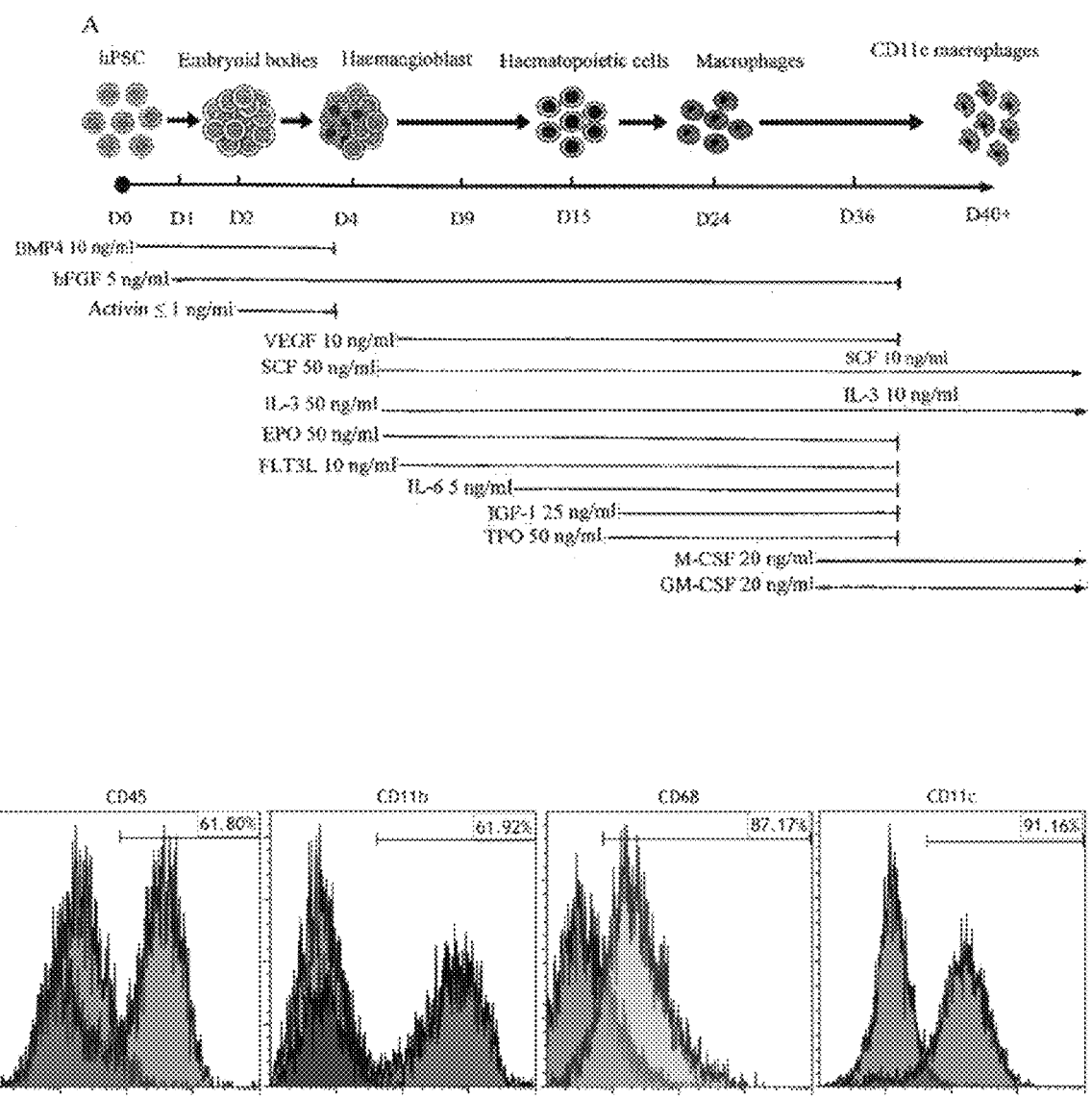
FIG. 14 depicts A) a schematic representation of macrophage differentiation of human pluripotent stem cells in a non-limiting embodiment, and B) the results of flow cytometry analysis of cells for expression CD45 (hematopoietic marker), CD11b (myeloid marker), CD68 (macrophage marker) and CD11c (alveolar macrophage marker).

After 3-5 weeks of culturing the cells, CD68 and CD11c expression were analyzed and confirmed by flow cytometry with human specific antibodies (FIG. 14B). Human alveolar-like macrophages were further characterized by surface markers. Flow cytometry was used to determine surface expression of the hematopoietic marker, CD45, the myeloid marker, CD11b, and the alveolar macrophage marker, CD11c, on cells and to rule out the presence of endothelial cells expressing CD34. Fluorescence microscopy of the cells also indicates the ability of cells to uptake DiI-AcLDL, a known function of macrophages.

Example 4

In Vitro-Derived Macrophages Genetically Altered to Express IL-10

A lentiviral transfer of the murine IL-10 gene using GeneCopoeia's EX-Mm03260-Lv201 lenti-vector to stem cell-derived alveolar-like macrophages (from human and mouse) was conducted as follows. In brief, the vector contained a CMV promoter driving the ORF of mouse IL10 (Accession: NM_010548.2) followed by SV40-eGFP-IRES-puromycin. To generate lentivirus, the HIV-based EX-Mm03260-Lv201 lenti-vector, in conjunction with GeneCopoeia's Lenti-Pac™ HIV Expression Packaging vectors were co-transfected into HEK293T cells using GeneCopoeia's EndoFectin™ Lenti Transfection Reagent. Cells were incubated in the presence of 5% CO2 at 37° C. overnight. Growth medium were changed to Opti-MEM containing 3% FBS with the addition of GeneCopoeia's Titerboost™.

Figure 15:
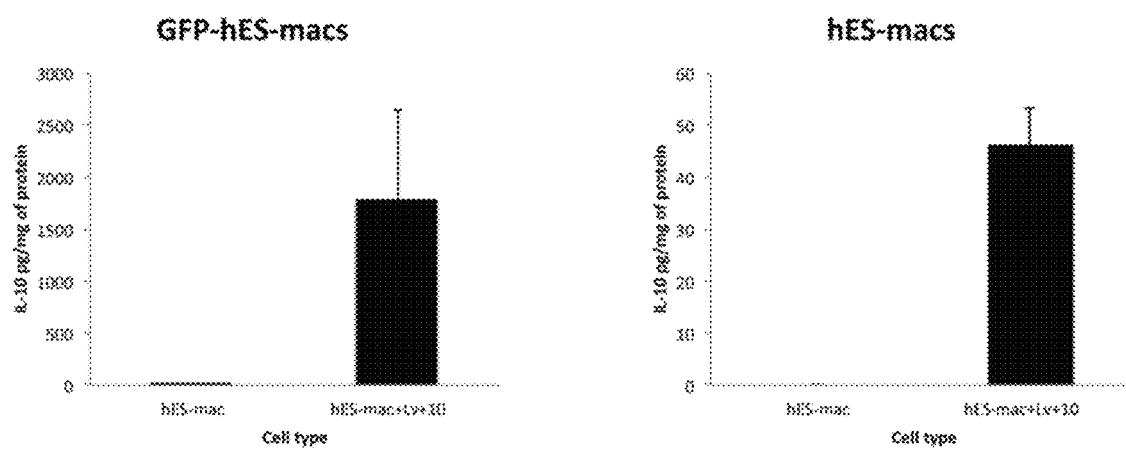
FIG. 15 graphically illustrates IL-10 protein secretion from lentiviral transfected human stem cell-derived alveolar-like macrophage cells.

Conditioned medium were collected after 24, 48 and 72 hours of incubation. Viral supernatant from transfected packaging cells was centrifuged at 2000×g for 30 minutes to remove any loose cells and cell debris, and was then transferred to new tube. PEG 6000 solution was then added to make the final PEG 6000 concentration, 8.5% and the final NaCl concentration, 0.3 M. The mixture was incubated on ice for 3 to 6 hours, then centrifuged at 2000×g for 30 minutes. The viral particle pellet was resuspended by pipetting in 1/20 of the original harvest volume of Opti-MEM. Infection of lentivirus was performed on a 24-well or 6-well plate. Target stem cell-derived alveolar-like macrophage cells were plated at least one day before infection at a cell density about 60-70% confluent. Appropriate amounts of concentrated viral particles were added to the target cells, together with polybrene, to a final concentration of 80 μg per milliliter. Growth medium were changed one to three days after infection. Mouse cells were selected under puromycin (0.75 μg per milliliter) for more than two weeks, positive cells were verified by GFP and IL-10 expression. Following selection, GFP-expressing cells were sorted using FACS analysis and expanded in DMEM/F12 with 10% FBS and 1% penicillin/streptomycin with 20 ng/ml of GM-CSF and 10 ng/ml of M-CSF. Cells were cultured until they were uniform for GFP expression. Secretion of IL-10 was confirmed using a cytokine ligand blot assay. For human stem cell-derived alveolar macrophages, transfection was confirmed successful by visually observing using fluorescent microscopy that some cells newly expressed the GFP reporter. Luminex Cytokine 1-Plex targeting IL-10 was also used. This confirmed in 2 independent human PSC cell lines that macrophages undergoing the transfection expressed the IL-10 gene product; whereas cells not undergoing the transfection did not express the IL-10 gene product (FIG. 15).

Example 5

In Vitro-Derived Macrophages Genetically Altered to Express A1AT

Figure 16:
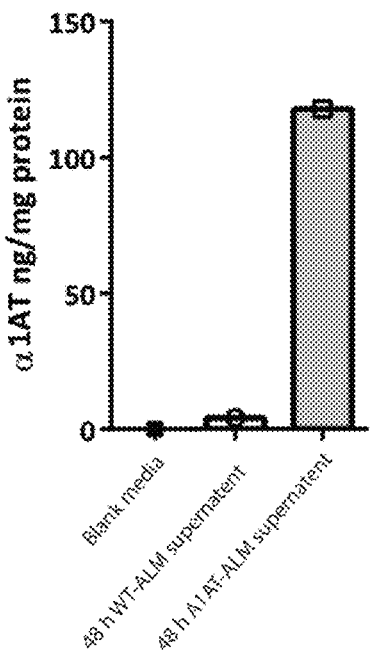
FIG. 16 graphically illustrates that lentiviral transfected human stem cell-derived alveolar-like macrophages (A1AT-ALMs) secrete human alpha-1-antitrypsin (A) that inhibits elastase activity (B), and A1AT-ALMs secrete A1AT protein in the airway fluid after their delivery directly to the airways (C).
Figure 16:
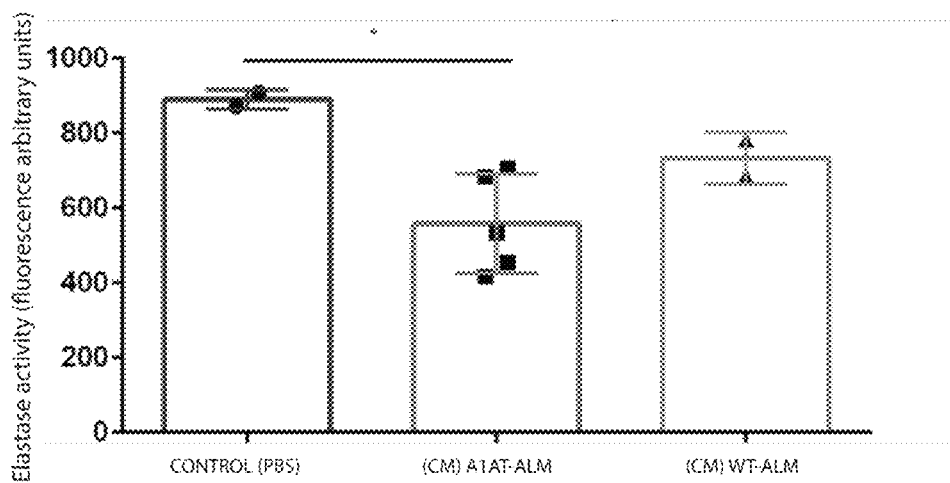
Figure 16:
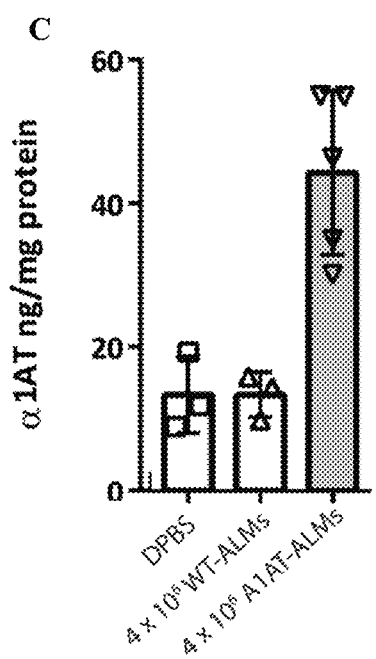

Mouse ALMs were genetically modified using lentiviral gene transductions (as described in Example 4) to express and secrete the protease inhibitor, human alpha-1-antitrypsin (A1AT). The modified ALMs were called A1AT-ALMs. To confirm that the A1AT-ALMs expressed A1AT, the conditioned media cell supernatants of wild-type (WT-) and A1AT-ALMs were collected after 48 hours of incubation and A1AT was quantified by ELISA, and substantial expression of A1AT was shown in the A1AT-ALM supernatant vs. the WT-ALM supernatant (FIG. 16A). Similarly, the WT-ALM and A1AT-ALM conditioned media supernatants were assessed for their ability to inhibit elastase activity, and A1AT-ALMs exhibited greater elastase inhibition as compared to WT-ALMs (FIG. 16B).

To confirm expression of A1AT by A1AT-ALMs in vivo, four million WT-ALMs or A1AT-ALMs or vehicle (DPBS) were intratracheally delivered to mouse airways and after 48 hours BAL fluid was collected and A1AT concentrations assessed by ELISA. Substantial expression of A1AT was shown in BAL fluid from A1AT-ALM mice vs. the expression of A1AT in BAL fluid from WT-ALM or control mice (FIG. 16C). Thus, ALMs genetically modified to express human alpha-1-antitrypsin (A1AT) secrete functional A1AT that inhibits elastase activity. Furthermore, the A1AT-ALMs secrete A1AT protein in the airway fluid following their delivery directly to the airways.

These data confirm that the present ALMs can be genetically modified to express functional protein.

Example 6

In Vitro-Derived Macrophages do not Induce Immune Response

No noticeable adverse effects from transplantation of PSC-AMs to non-strain matched mice have been observed. Therefore, it was determined whether or not mouse PSC-AMs would be accepted by the airways of rats. $5 \times 10^6$ PSC-AMs suspended in a 300 μl bolus of DPBS was instilled directly into the airways of adult rats. The rats were monitored daily for 14 days. After a brief recovery period immediately following cell administration, all animals receiving mouse PSC-AMs continued to thrive and gained weight in equal proportions to their PBS-treated counterparts. Two weeks (14 days) following PSC-AM delivery, the rats were sacrificed for pulmonary examination. No evidence of extended injury was detectable.

Example 7

H1 human embryonic stem cells were used as a source to produce alveolar-like macrophages using the serum-free factor-defined differentiation protocol described in Example 3.

After 5 weeks of culturing the cells, flow cytometry was used as above to confirm the presence of myeloid and alveolar markers, including CD45, CD11b, CD11c, CD206, CD169 and CD163, using human specific antibodies.

Fluorescence microscopy of the cells also indicates the ability of the cells to uptake DiI-AcLDL. It was also confirmed that these alveolar-like macrophages internalize green fluorescent *Staphylococcus aureus* at 5 weeks and furthermore at 8 weeks even after subsequent passaging.

The proliferative capacity of the cells was also evaluated. Firstly, reproducible differentiations were performed that can be achieved within 5 weeks of induction. Additionally, it was determined that the alveolar-like macrophages are proliferative, maintain expansion capabilities after 5 weeks of culturing, and expand with a doubling time of about 2 days in serum-free medium containing 100 ng/ml GM-CSF, 50 ng/ml M-CSF and 50 ng/ml IL-3 after 5 weeks of culturing.

Example 8

The following was conducted to demonstrate that the present PSC-AMs exhibit prolonged proliferation capacity under in vitro conditions which is not exhibited by primary alveolar macrophages (AMs). The proliferation rate of freshly isolated mouse and rat primary alveolar macrophages were compared to that of mouse and rat alveolar macrophage-like cells prepared as described in Example 1. Primary AMs were collected by bronchoalveolar lavage of 4 rats and 5 mice, respectively, and incubated in media conditions, outlined in Nakata et al., 1991, over a seven-day period. Mouse and rat PSC-AMs were also cultured under the same conditions. The doubling rate of rat and mice PSC-AMs was 34.2 and 46.4 hours, respectively, while rat and mice primary AMs did not proliferate, and the number of cells decreased over time. The experiment was terminated at seven days as the PSC-AMs overgrew the culture dish at this point, but after passaging, the PSC-AMs continued to proliferate. In fact, these cells continued to proliferate, with subsequent passaging, for more than 1 year without losing their phenotypic characteristics. This data confirms that the growth characteristics of the present AMLs differ substantially to AMs in that they exhibit prolonged proliferation under the same conditions.

DISCUSSION

Pluripotent stem cells were used to generate Myb-independent macrophages from yolk-sac hematopoiesis that were conditioned in vitro to be tissue-specific and 'alveolar-like' to produce a cell more representative of a long living primary resident AM. Generation of these PSC-AMs is rapid and efficient; producing at least $6 \times 10^5$ cells per 1 million undifferentiated starting cells. This can be scaled up or down and the resultant cells are expandable for more than 1 year or can be cryopreserved without notable phenotypic changes. The PSC-AMs express and retain the distinguishing ligand markers F4/80, CD11c and SiglecF of primary AMs, without expressing markers of other cells types like MHCII or Langerin, while exhibiting functional qualities like primary AMs both in vitro and in vivo. Additional characterization of the PSC-AM indicates that these cells exhibit an M1-polarization phenotype when evaluated for basal level secreted cytokines. Pulmonary transplantation of only $5 \times 10^5$ PSC-AMs to healthy mice revealed retention of the cells in the airways for several weeks with no obvious transplantation associated injury or immune suppression requirement. The PSC-AMs can persist in the airways during acute lung injury and display immediate and sustained functional phagocytosis of host-derived cellular debris and bacteria in vivo. Most notably, was the remarkable contribution that PSC-AMs made to the regeneration and recovery of the pulmonary pathology typically exhibited in $ADA^{-/-}$ mice.

It is noted that the foregoing has outlined some of the more pertinent non-limiting embodiments. It will be clear to those skilled in the art that modifications to the disclosed non-limiting embodiment(s) can be effected without departing from the spirit and scope thereof. As such, the described non-limiting embodiment(s) ought to be considered to be merely illustrative of some of the more prominent features and applications. Other beneficial results can be realized by applying the non-limiting embodiments in a different manner or modifying them in ways known to those familiar with the art. The mixing and matching of features, elements and/or functions between various non-limiting embodiment(s) is expressly contemplated herein so that one of ordinary skill in the art would appreciate from this disclosure that features, elements and/or functions of one embodiment may be incorporated into another embodiment as appropriate, unless described otherwise, above. Although the description is made for particular arrangements and methods, the intent and concept thereof may be suitable and applicable to other arrangements and applications.

Relevant portions of references referred to herein are incorporated by reference.

What is claimed is:

1. A method of generating alveolar macrophages, the method comprising:
   i) culturing mammalian hemangioblasts in medium comprising vascular endothelial growth factor (VEGF), stem cell factor (SCF), interleukin 6 (IL6), and interleukin 3 (IL3) such that macrophages are obtained;
   ii) culturing the macrophages in medium comprising granulocyte macrophage colony stimulating factor (GM-CSF), macrophage colony stimulating factor (M-CSF), IL3, and SCF such that alveolar macrophages are obtained.

2. The method of claim 1, wherein the amount of each of GM-CSF and M-CSF is about 10-100 ng/ml.

3. The method of claim 1, wherein the medium of step i) comprises about 5-50 ng/ml VEGF; about 10-100 ng/ml IL-3; and about 10-100 ng/ml SCF.

4. The method of claim 1, wherein step i) comprises:
   a) culturing mammalian pluripotent cells in serum-free differentiation medium such that embryoid bodies (EBs) are obtained; and
   b) culturing the EBs in medium comprising bone morphogenic factor 4 (BMP4) and Activin-A, and optionally fibroblast growth factor (FGF) such that hemangioblasts are obtained.

5. The method of claim 1, further comprising: iii) expanding said alveolar macrophages in medium containing about 10-50 ng/ml GM-CSF and about 10-50 ng/ml M-CSF.

6. The method of claim 1, wherein the medium of step i) additionally comprises one or more of thrombopoietin (TPO), Fms-related tyrosine kinase 3 ligand (FLT3L) and insulin-like growth factor (IGF-1).

* * * * *